(12) United States Patent
Thomas et al.

(10) Patent No.: US 7,662,973 B2
(45) Date of Patent: Feb. 16, 2010

(54) FLUORESCENT DETECTION METHOD AND REAGENT

(75) Inventors: Nicholas Thomas, Whitchurch (GB); Nigel Paul Michael, Whitchurch (GB); Valerie Millar, Whitchurch (GB); Beth Davies, Whitchurch (GB); Mark Samuel Jonathan Briggs, Whitchurch (GB)

(73) Assignee: GE Healthcare UK Limited, Amersham (GB)

( * ) Notice: Subject to any disclaimer, the term of this patent is extended or adjusted under 35 U.S.C. 154(b) by 862 days.

(21) Appl. No.: 10/182,996

(22) PCT Filed: Feb. 1, 2001

(86) PCT No.: PCT/GB01/00396

§ 371 (c)(1),
(2), (4) Date: Oct. 16, 2002

(87) PCT Pub. No.: WO01/57237

PCT Pub. Date: Aug. 9, 2001

(65) Prior Publication Data

US 2003/0186348 A1 Oct. 2, 2003

(30) Foreign Application Priority Data

Feb. 2, 2000 (GB) .................................. 0002261.6

(51) Int. Cl.
*C09B 7/02* (2006.01)

(52) U.S. Cl. .................................................. 548/457
(58) Field of Classification Search ................. 548/457, 548/459

See application file for complete search history.

(56) References Cited

U.S. PATENT DOCUMENTS 5,658,751 A    8/1997    Singer et al.
5,780,585 A    7/1998    Springer et al.

OTHER PUBLICATIONS

Bridgewater et al., Eur. J. of Cancer (1995), vol. 31A(13/14), pp. 2362-2370.*
Blomberg, K., et al. "Time-resolved fluorometric assay for natural killer activity using target cells labelled with a fluorescence enhancing ligand" Journal of Immunological Methods, Elsevier Science Publishers B.V., Amsterdam, NL vol. 193, No. 2, Jun. 21, 1996 pp. 199-206.
R. E. Bareiss; J. Kahovec; and P. Kratochvil, "Graphic Representations (Chemical Formulae) of Macromolecules", Pure and Applied Chemistry, vol. 66, No. 12, pp. 2469-2482 (1994).

* cited by examiner

*Primary Examiner*—Taofiq A Solola
(74) *Attorney, Agent, or Firm*—Yonggang Ji

(57) ABSTRACT

Disclosed is a method for increasing the fluorescence of a Cyanine dye molecule comprising at least one $NO_2$ group characterized by the reduction of the at least one $NO_2$ group to NHOH or $NH_2$ by the action of a nitroreductase. The cyanine dye molecule comprising at least one $NO_2$ group can be used as a substrate for detecting nitroreductase enzyme activity in a composition and allows for the use of a nitroreductase enzyme in an enzyme-reporter system for the detection of analytes, binding reactions or gene expression.

6 Claims, 14 Drawing Sheets

1a

CY-Q F

1b

2a

CY-Q G

2b

Cy5Q

FLUORESCENT DETECTION METHOD AND REAGENT

The present invention relates to methods for generating molecules with a high fluorescence output from molecules with a lower or negligible fluorescence and which may be catalysed by enzymatic action. In particular, the invention relates to methods for achieving fluorescence detection of analytes by using enzymatic means to generate fluorescent reporter molecules.

The use of fluorescence as a detection modality in biological assays is widespread, and a diverse variety of procedures are available to generate fluorescence in assay conditions for detection by a wide range of techniques. These techniques include fluorescence microscopy, fluorescence immunoassay and flow cytometry.

Among the methods used to generate a fluorescent signal are those which use an enzyme to convert a non-fluorescent substrate to a fluorescent product.

The enzyme may be coupled to an assay component, for example to an antibody in an immunoassay or to a nucleic acid molecule in a nucleic acid hybridisation assay, and is typically used to generate a fluorescence signal from a non-fluorescent substrate. In such methods, the fluorescence intensity of the product provides the assay signal, and correlates with the amount of analyte in the assay (e.g. an antigen in an immunoassay or a complementary nucleic acid sequence in a nucleic acid hybridisation assay). Examples of such enzyme based fluorescence method assays are described in "Applications of Fluorescence in Immunoassays", Chapter 9, pages 223-232, I. A. Hemmila, John Wiley & Sons, New York, 1991 (immunoassays) and "Nonisotopic DNA Probe Techniques", Chapter 1, pages 3-23, L. J. Kricka, Academic Press Inc., New York, 1992 (nucleic acid hybridisation assays) and enzymes used in such assays include Horse Radish Peroxidase (HRP) and alkaline phosphatase.

Alternatively, the enzyme may be generated by protein synthesis in the course of the assay. For example, in an in vivo gene expression assay the enzyme is synthesised from a gene, usually termed a reporter gene, which is inserted into a cell or organism in which it does not occur naturally or is only found at low levels, in such a way that expression of the reporter gene is linked to the expression of a cellular gene of interest. Consequent processing of the enzyme's non-fluorescent substrate to a fluorescent product correlates with the expression of the reporter gene, and hence provides an indirect measure of the expression of the cellular gene of interest. Enzymes that are synthesised from reporter genes and currently used in fluorescent assays for the measurement of in vivo gene expression include β-galactosidase, alkaline phosphatase and β-lactamase.

β-galactosidase is a bacterial enzyme and has been well characterised for use in such enzyme-reporter assays in combination with substrates which can be rendered fluorescent by enzyme activity. The detection of β-galactosidase expression is described in "Fluorescence Microscopy and Fluorescent Probes", pages 211-215, J. Slavik, Plenum Press, London, 1996. Here, a non-fluorescent substrate, CMFDG, is microinjected into cells expressing the enzyme where it is hydrolysed into a fluorescent form giving a measure of enzyme activity. However, as mammalian cells display some endogenous β-galactosidase activity, some background fluorescence of the converted substrate is observed in in vivo assays for gene expression even in the absence of signals leading to the expression of β-galactosidase from the reporter gene.

Mammalian cells can also have some endogenous alkaline phosphatase enzyme activity again leading to a background of activation of a non-fluorescent substrate into its fluorescent form in in vivo assays based on alkaline phosphatase expression. In this case, the fluorescent substrate is, typically, fluorescein diphosphate. In addition, optimal alkaline phosphatase activity requires pH 9.8 which limits the use of this enzyme in in situ assays.

More recently, a fluorescent substrate for β-lactamase has been documented (see U.S. Pat. No. 5,955,604, Tsien et al.). The substrate described therein, CCF2, is suitable for use in a FRET based assay (as described below) in which the donor and acceptor molecules in the fluorescent substrate are separated by the enzyme activity of β-lactamase to generate a fluorescent signal from the donor molecule.

However, the fluorochromes used in these techniques are, typically, fluorescein and its derivatives (Handbook of Fluorescent Probes and Research Chemicals, Molecular Probes, $6^{th}$ Edition, 1996 or see www.probes.com). Fluorescein-based fluorochromes typically have excitation wavelengths in the WV to blue region of the spectrum and emission wavelengths in the blue to green region of the spectrum (i.e. excitation at approx. 488 nm and emission at approx. 510 nm). These characteristics confer certain restrictions on the use of these fluorochromes with biological materials as these wavelengths coincide with the excitation and emission ranges of a number of biological molecules. This can give high background fluorescence in biological assays with a resultant reduced sensitivity of detection.

Moreover, as all these known techniques yield signals within the same region of the spectrum, there is limited scope for multiple signalling systems being employed and read simultaneously.

Dyes based on fluorescein have a number of other disadvantages, including their tendency to photobleach when illuminated by strong excitation sources. Furthermore, some products from enzyme substrates based on these fluorochromes are pH sensitive, which can lead to variation in fluorescence in different environments. Problems may arise using these fluorochromes in intracellular assays as excitation in the UV region, requiring high energy excitation at a short wavelength, may give rise to cell damage which can, in turn, lead to misleading results.

To overcome these shortcomings of existing enzyme fluorescence substrates, there is a requirement for a molecule (or molecules) which is the substrate for a non-ubiquitous enzyme and which has zero or low fluorescence in a first form and which, on reaction with the enzyme, yields an environmentally stable fluorescent product which can emit light over a broad range of the spectrum. The range of emission could be, for example in the range of 500-900 nm region of the spectrum.

The Cyanine dyes (sometimes referred to as "Cy dye™"), described, for example, in U.S. Pat. No. 5,268,486, are a series of biologically compatible fluorophores which are characterised by high fluorescence emission, environmental stability and a range of emission wavelengths extending into the near infra-red which can be selected by varying the internal molecular skeleton of the fluorophore.

Recently, cyanine dyes have been developed for use in Fluorescence Resonance Energy Transfer (FRET) assays. The principal of FRET was described in U.S. Pat. No. 4,996, 143 and, more recently, in PCT/GB99/01746 (publication number WO99/64519). Briefly, FRET assays depend on an interaction between two fluorophores, a donor fluorophore and an acceptor fluorophore. When the donor and acceptor molecules are in close enough proximity, the fluorescence of the donor molecule is transferred to the acceptor molecule with a resultant decrease in the lifetime and a quenching of fluorescence of the donor species and a concomitant increase in the fluorescence intensity of the acceptor species. The use of FRET labels in biological systems is well known. The principle has been used in the detection of binding events or cleavage reactions in assays which employ FRET. In the case of peptide cleavage reactions, a fluorescent donor molecule and a fluorescent acceptor molecule are attached to a peptide substrate on either side of the peptide bond to be cleaved and at such a distance that energy transfer takes place. A peptide cleavage reaction will separate the donor and acceptor molecules and thus the fluorescence of the donor molecule will be restored.

In one format of this principle, a fluorescent moiety is caused to be in close proximity with a "quencher" molecule such that the energy from the excited donor fluorophore is transferred to the quencher and dissipated as heat rather than fluorescence energy. In this case, residual fluorescence is minimised when the two components of the donor-quencher pair are in close proximity and a large change in signal can be obtained when they are separated.

Cyanine dyes suitable for use as acceptor or "quencher" molecules in a FRET assay have been developed (see PCT/GB99/01746) by making certain modifications to cyanine dyes through introduction of chemical groups which have the effect of diminishing or abolishing the fluorescence of the molecule. One example of such a chemical modification is the introduction of —$NO_2$ groups. Such quenched Cy dyes are referred to as Cy-Q dyes or "dark dyes".

The bacterial enzymes termed nitroreductases have been shown to catalyse the general reaction set out below in reaction scheme 1:

Reaction Scheme 1

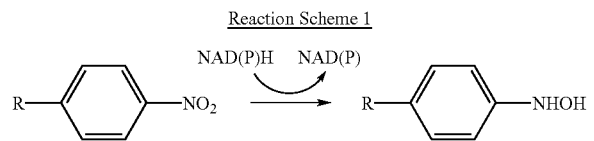

where, in the presence of NADH or NADPH, one or more —$NO_2$ groups on an organic molecule are reduced to a hydroxylamine group which may subsequently be converted to an amine group. Bacterial nitroreductases have been used, in anti-tumour therapy, to convert prodrug molecules into their corresponding cytotoxic forms (Anlezark et al 1995, Biochem-Pharmacol 50(5), 609-18) by removing or reducing one or more —$NO_2$ groups on the prodrug substrate. Such substrates include p-nitrobenzyloxycarbonyl derivatives of cytotoxic compounds. Selective killing of tumour cells can be achieved by targeting expression of the nitroreductase gene to tumour cells and administering the prodrug to the affected tissue (as described, for example, in U.S. Pat. No. 5,780,585). The prodrug substrate is converted to its cytotoxic form in the tumour cells expressing nitroreductase while the surrounding cells (which do not contain the nitroreductase) remain unaffected.

Nitroreductases have also been used in bio-remediation processes for clearing nitroaromatic compounds which may create environmental or health hazards. U.S. Pat. No. 5,777,190 describes a catalytic method involving oxygen-sensitive nitroreductases for reducing nitroaromatic compounds which may be controlled, to prevent the reaction from progressing to completion, by the addition of oxygen. Suggested substrates include nitrobenzene, trinitrotoluene and orthochloronitrobenzene with preferred oxygen sensitive nitroreductase enzymes including ferredoxin NADP, xanthine oxidase and glutathione reductase.

To date, there appear to be no reports that an $NO_2$-containing modified cyanine dye molecule could act as a substrate for a nitroreductase to generate a fluorescent molecule.

The present invention provides a method for increasing fluorescence of a modified cyanine dye comprising at least one $NO_2$ (nitro) group, for example, a Cy-Q dye. This can be achieved by enzymatic conversion of an $NO_2$ group in such a Cy-Q dye to a NHOH or $NH_2$ by the action of a nitroreductase (NTR). Depending on the structure of the Cy-Q dye, the fluorescence emission from the product of the Cy-Q/NTR reaction may occur across a wide range of wavelengths, typically 500-900 nm, in contrast to existing reporters which emit only in the blue-green region of the spectrum. This emission at longer wavelengths is advantageous in avoiding background fluorescence and increasing sensitivity in biological systems.

Moreover, the fluorescence emission characteristics of the Cy-Q/NTR reaction product can be altered to suit the application by making changes to the internal structure of the Cy-Q molecule, without changing the extremities of the molecule, e.g. the $NO_2$ groups, that are involved in reaction with nitroreductase. Thus, fluorescent reporters compatible for use with other fluors in multiplex systems can be provided.

In addition, the structure-defined emission characteristics of the Cy-Q make it suitable for inclusion in a paired fluorophore ratiometric reporter molecule where one member of the pair is a fluorescent dye and the second member is a Cy-Q dye. Nitroreductase action on the Cy-Q leads to a change in the ratio of fluorescence emission from the two fluors when excited and monitored at two different wavelengths. Such a ratiometric reporter molecule allows measurement of enzyme activity to be made independent of the concentration of the reporter molecule.

The invention accordingly provides in a first aspect, a method for increasing the fluorescence of a dye molecule comprising at least one $NO_2$ group characterised by the reduction of said at least one $NO_2$ group to NHOH or $NH_2$.

Suitable $NO_2$-containing dyes include fluorescent dyes such as cyanine derivates, Cy-Q (described in PCT/GB99/017460), $NO_2$-lanthanide chelates (described, for example, in Latra, M. J., Lumin. 1997, 75, 149-169 and Blasse, G., J. Phys. Chem. 1998; 92; 2419-2422) and $NO_2$-containing fluoresceins, pyrenes, rhodamines, coumarins or BODIPY™ dyes.

In one embodiment of the first aspect, the dye molecule comprising at least one $NO_2$ group for use in the present invention is a modified cyanine dye compound having the Formula I:

(Formula I)

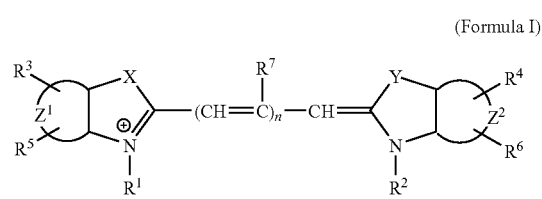

wherein groups $R^3$, $R^4$, $R^5$ and $R^6$ are attached to the rings containing X and Y or, optionally, are attached to atoms of the $Z^1$ and $Z^2$ ring structures and n is an integer from 1-3;

$Z^1$ and $Z^2$ each represent a bond or the atoms necessary to complete one or two fused aromatic rings each ring having five or six atoms, selected from carbon atoms and, optionally, no more than two oxygen, nitrogen and sulphur atoms;

X and Y are the same or different and are selected from bis-$C_1$-$C_4$ alkyl- and $C_4$-$C_5$ spiro alkyl-substituted carbon, oxygen, sulphur, selenium, —CH=CH— and N—W wherein N is nitrogen and W is selected from hydrogen, a group —$(CH_2)_m R^8$ where m is an integer from 1 to 26 and $R^8$ is selected from hydrogen, amino, aldehyde, acetal, ketal, halo, cyano, aryl, heteroaryl, hydroxyl, sulphonate, sulphate, carboxylate, phosphonate, polyethylene glycol, substituted amino, quaternary ammonium, nitro, primary amide, substituted amide, and groups reactive with amino, hydroxyl, carbonyl, carboxyl, phosphoryl, and sulphydryl groups;

groups $R^3$, $R^4$, $R^5$, $R^6$ and $R^7$ are independently selected from the group consisting of hydrogen, substituted or unsubstituted $C_1$-$C_4$ alkyl, $OR^9$, $COOR^9$, nitro, amino, acylamino, quaternary ammonium, phosphate, sulphonate and sulphate, where $R^2$ is substituted or unsubstituted and selected from H, $C_1$-$C_4$ alkyl, amino, aldehyde, acetal, ketal, halo, cyano, aryl, heteroaryl, hydroxyl, sulphonate, sulphate, carboxylate, substituted amino, quaternary ammonium, nitro, primary amide, substituted amide, and groups reactive with amino, hydroxyl, carbonyl, carboxyl, phosphoryl, and sulphydryl groups;

groups $R^1$ and $R^2$ are selected from $C_1$-$C_{10}$ alkyl which may be unsubstituted or substituted;

characterised in that at least one of the groups $R^1$, $R^2$, $R^3$, $R^4$, $R^5$, $R^6$ and $R^7$ comprises at least one nitro group which reduces the fluorescence emission of said dye such that it is essentially non-fluorescent.

Suitably, the at least one nitro group comprised in the dyes of Formula I may be attached directly to the rings containing X and Y. In the alternative, a mono- or di-nitro-substituted benzyl group may be attached to the rings containing X and Y, which optionally may be further substituted with one or more nitro groups attached directly to the aromatic rings.

In one embodiment, $R^1$ and $R^2$ may be selected from $C_1$-$C_{10}$ alkyl which may be substituted with groups including $NH_2$, OH, COOH, $SO_3H$, $PO_4H$, SH, polyethylene glycol and phenyl. Where phenyl is substituted, it may optionally be substituted by up to two substituents selected from carboxyl, sulphonate and nitro groups.

Examples of the non-fluorescent cyanine dye molecules suitable for use in the present invention have either Formula II and Formula III:

Formula II

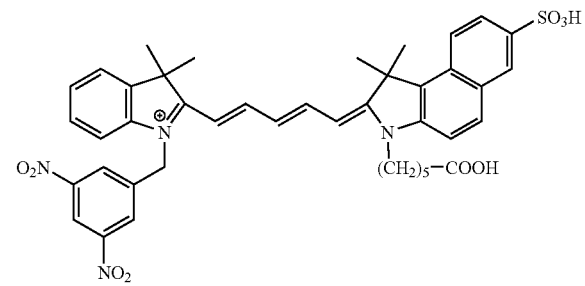

-continued

Formula III

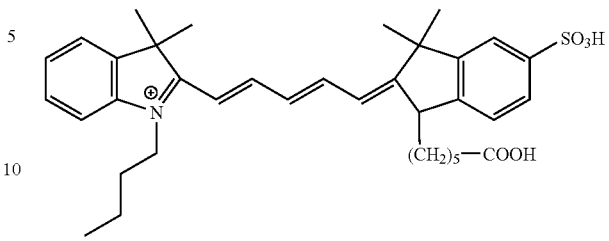

Especially preferred are $NO_2$-containing "dark dye" forms of any of the following Cy dyes. The excitation (Abs) and emission (Em) characteristics of the unmodified dye molecules are shown:

| Dye | Fluorescence Colour | Abs (nm) | Em (nm) |
| --- | --- | --- | --- |
| Cy2 | Green | 489 | 506 |
| Cy3 | Orange | 550 | 570 |
| Cy3.5 | Scarlet | 581 | 596 |
| Cy5 | Far red | 649 | 670 |
| Cy5.5 | Near-IR | 675 | 694 |
| Cy7 | Near-IR | 743 | 767 |

In another embodiment of the first aspect, the reduction of a $NO_2$ group is catalysed by an enzyme, which can be a nitroreductase and, preferably, a bacterial nitroreductase.

Importantly, this means that cyanine-based dyes can be used in such an enzyme-substrate reaction at the same time as any of the conventional enzyme-substrate reactions which give a fluorescence readout in the blue/green region of the spectrum. Measurements can be made simultaneously using two different wavelengths; for example, fluorescein-based molecules could be detected at Abs 488/Em 510 whereas reduced cyanine-based molecules, such as those based on Cy5, could be detected at Abs 649/Em 670. This would allow multiplexing i.e. measuring a number of different in vitro or in vivo effects simultaneously.

$NO_2$-containing cyanine molecules can be described as "non-fluorescent dyes" i.e. those dyes which have an intrinsic low efficiency for converting absorbed incident light into fluorescence. The effectiveness of a non-fluorescent dye as a nitroreductase substrate is the extent to which it can convert incident light to fluorescence after a reduction reaction.

An increase in fluorescence can be measured relative to a control sample comprising an $NO_2$-containing cyanine dye molecule substrate in the absence of a nitroreductase enzyme.

In a second aspect of the invention there is provided a method for detecting nitroreductase enzyme activity in a composition comprising:

a) mixing said composition with a dye compound comprising at least one $NO_2$ group under conditions to promote nitroreductase activity; and b) measuring an increase in fluorescence wherein said increase is a measure of the amount of nitroreductase activity.

In a particularly preferred embodiment, the dye compound is a cyanine dye compound comprising at least one $NO_2$ group.

Suitably the cyanine dye compound is a compound of Formula I as hereinbefore described.

In one embodiment of the second aspect, the composition comprises a cell or cell extract. In principle, any type of cell can be used i.e. prokaryotic or eukaryotic (including bacterial, mammalian and plant cells). Where appropriate, a cell extract can be prepared from a cell, using standard methods known to those skilled in the art (Molecular Cloning, A Laboratory Manual $2^{nd}$ Edition, Cold Spring Harbour Laboratory Press 1989), prior to measuring fluorescence.

Typical conditions for nitroreductase activity comprise incubation of the composition and a cyanine dye molecule comprising at least one $NO_2$ group at approximately 37° C. in the presence of NADH and FMN.

In a third aspect of the invention there is provided a method of detecting analytes comprising;
a) providing a nitroreductase enzyme coupled to an assay reagent under conditions where the amount of activity of the enzyme is proportional to the amount of analyte in the assay;
b) providing a dye compound comprising at least one $NO_2$ group; and
c) measuring an increase in fluorescence as a measure of the amount of nitroreductase activity.

In a fourth aspect of the invention there is provided an assay method which comprises:
a) binding a first component of a specific binding pair to a surface;
b) adding a second component of the specific binding pair under conditions to promote binding between the components, said second component being labelled with a nitroreductase enzyme;
c) adding a dye compound comprising at least one $NO_2$ group under conditions suitable for nitroreductase activity; and
d) detecting binding of the second component to the first component by measuring an increase in fluorescence as a measure of bound nitroreductase activity.

In a particularly preferred embodiment of the third or fourth aspects of the invention, the dye compound is a cyanine dye compound comprising at least one $NO_2$ group.

Suitably, the dye compound employed in the third or fourth aspects is a cyanine dye compound of Formula I as hereinbefore described.

In one embodiment of the fourth aspect, said specific binding pair is selected from the group consisting of antibodies/antigens, lectins/glycoproteins, biotin/streptavidin, hormone/receptor, enzyme/substrate, DNA/DNA, DNA/RNA, DNA/binding protein or engineered binding partner.

Briefly, an in vitro assay method for the detection of antibody binding may be configured as follows. An antibody specific for an antigen of interest may be labelled by covalently linking it to an enzymatically active nitroreductase. Said labelled antibody can then be introduced into the test sample containing the antigen under binding conditions. After washing to remove any unbound antibody, the amount of antibody bound is detected by incubating the sample with the non-fluorescent cyanine dye substrate under conditions for nitroreductase activity and measuring an increase in fluorescence. The amount of fluorescence detected will be proportional to the amount of nitroreductase-labelled antibody that has bound to the analyte.

In an in vitro assay for detecting the binding of nucleic acids by hybridisation, either of the pair of target and probe nucleic acid is bound to a membrane or surface. The unbound partner is labelled with nitroreductase and incubated under hybridising conditions with the bound nucleic acid. Unbound, labelled nucleic acid is washed off and the amount of bound, labelled nucleic acid is measured by incubating the membrane or surface with a non-fluorescent cyanine dye under conditions suitable for nitroreductase activity. The amount of increase in fluorescence gives a measure of the amount of bound labelled DNA.

Methods for coupling enzymes to other biomolecules, e.g. proteins and nucleic acids, are well known. (Bioconjugate Techniques, Academic Press 1996). Coupling may be achieved by direct means, for example by use of a suitable bifunctional crosslinking agent (e.g. N-[β-Maleimidopropionic acid]hydrazine, Pierce) to covalently link the enzyme and binding partner. Alternatively, coupling may be achieved by indirect means, for example by separately biotinylating the enzyme and the binding partner using a chemically reactive biotin derivative, (e.g. N-hydroxysuccinimido-biotin, Pierce) and subsequently coupling the molecules through a streptavidin bridging molecule.

Cell based assays are increasingly attractive over in vitro biochemical assays for use in high throughput screening (HTS). This is because cell based assays require minimal manipulation and the readouts can be examined in a biological context that more faithfully mimics the normal physiological situation. Such in vivo assays require an ability to measure a cellular process and a means to measure its output. For example, a change in the pattern of transcription of a number of genes can be induced by cellular signals triggered, for example, by the interaction of an agonist with its cell surface receptor or by internal cellular events such as DNA damage. The induced changes in transcription can be identified by fusing a reporter gene to a promoter region which is known to be responsive to the specific activation signal.

In fluorescence-based enzyme-substrate systems, an increase in fluorescence gives a measure of the activation of the expression of the reporter gene.

Accordingly, in a fifth aspect of the invention, there is provided an assay method which comprises:
a) contacting a host cell with a dye compound comprising at least one $NO_2$ group, wherein said host cell has been transfected with a nucleic acid molecule comprising expression control sequences operably linked to a sequence encoding a nitroreductase; and
b) measuring an increase in fluorescence as a measure of nitroreductase gene expression.

In a particularly preferred embodiment, the dye compound is a cyanine dye compound comprising at least one $NO_2$ group. Suitably, the cyanine dye is a compound of Formula I as hereinbefore described.

Methods for using a variety of enzyme genes as reporter gene in mammalian cells are well known (for review see Naylor L. H. (1999) Biochemical Pharmacology 58, 749-757). The reporter gene is chosen to allow the product of the gene to be measurable in the presence of other cellular proteins and is introduced into the cell under the control of a chosen regulatory sequence which is responsive to changes in gene expression in the host cell. Typical regulatory sequences include those responsive to hormones, second messengers and other cellular control and signalling factors. For example, agonist binding to seven transmembrane receptors is known to modulate promoter elements including the cAMP responsive element, NFAT, SRE and AP1; MAP kinase activation leads to modulation of SRE leading to Fos and Jun transcription; DNA damage leads to activation of transcription of DNA repair enzymes and the tumour suppressor gene p53. By selection of an appropriate regulatory sequence the reporter gene can be used to assay the effect of added agents or cellular processes involving the chosen regulatory sequence under study.

For use as a reporter gene, the nitroreductase gene may be isolated by common methods, for example by amplification from a cDNA library by use of the polymerase chain reaction (PCR) (Molecular Cloning, A Laboratory Manual $2^{nd}$ Edition, Cold Spring Harbour Laboratory Press 1989 pp 14.5-14.20). Once isolated, the nitroreductase gene may be inserted into a vector suitable for use with mammalian promoters (Molecular Cloning, A Laboratory Manual $2^{nd}$ Edition, Cold Spring Harbour Laboratory Press 1989 pp 16.56-16.57) in conjunction with and under the control of the gene regulatory sequence under study. The vector containing the nitroreductase reporter and associated regulatory sequences may then be introduced into the host cell by transfection using well known techniques, for example by use of DEAE-Dextran or Calcium Phosphate (Molecular Cloning, A Laboratory Manual $2^{nd}$ Edition, Cold Spring Harbour Laboratory Press 1989 pp 16.30-16.46). Other suitable techniques will be well known to those skilled in the art.

Nitroreductase has been shown to be retained in cells when expressed in this manner (see Bridgewater et al. Eur. J. Cancer 31a, 2362-70).

In a preferred embodiment of the fifth aspect of the invention, the cyanine dye molecule comprising at least one $NO_2$ group is permeable to cells. Preferably, at least one of groups $R^1$, $R^2$, $R^3$, $R^4$, $R^5$, $R^6$ and $R^7$ of the cyanine dye molecule of Formula I comprises a cell membrane permeabilising group. Membrane permeant compounds can be generated by masking hydrophilic groups to provide more hydrophobic compounds. The masking groups can be designed to be cleaved from the fluorogenic substrate within the cell to generate the derived substrate intracellularly. Because the substrate is more hydrophilic than the membrane permeant derivative it is then trapped in the cell. Suitable cell membrane permeabilising groups may be selected from acetoxymethyl ester which is readily cleaved by endogenous mammalian intracellular esterases (Jansen, A. B. A. and Russell, T. J., J. Chem Soc. 2127-2132 (1965) and Daehne W. et al. J. Med-.Chem. 13, 697-612 (1970)) and pivaloyl ester (Madhu et al., J. Ocul. Pharmacol. Ther. 1998, 14, 5, pp 389-399) although other suitable groups including delivery molecules (such as delivery peptides) will be recognised by those skilled in the art.

In a sixth aspect of the invention there is provided an $NO_2$-containing compound in accordance with Formula I wherein said compound has been modified so as to be capable of entering a cell. Accordingly, in a particularly preferred embodiment, there is provided an $NO_2$-containing compound selected from compounds of Formula IIIa or Formula IIIb.

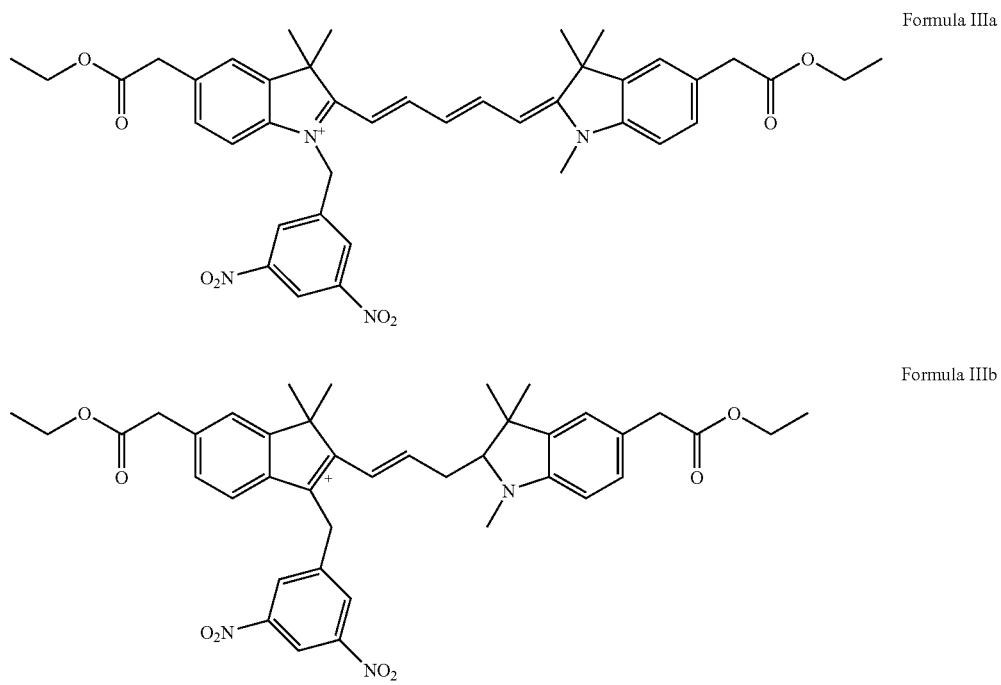

Typically, to assay the activity of an agent to activate cellular responses via the regulatory sequence under study, cells transfected with the nitroreductase reporter are incubated with the test agent, followed by addition of a cell-permeant cyanine dye substrate, such as a cyanine dye molecule comprising at least one $NO_2$ group. After an appropriate period required for conversion of the cyanine dye substrate to a form showing higher fluorescence, the fluorescence emission from the cells is measured at a wavelength appropriate for the chosen cyanine dye. For example, for the compound Cy-Q F (shown in FIG. 1a), fluorescence emission would be monitored at 690 nm with excitation at 650 nm. Measurement of fluorescence may be readily achieved by use of a range of detection instruments including fluorescence microscopes (e.g. LSM 410, Zeiss), microplate readers (e.g. CytoFluor 4000, Perkin Elmer), CCD imaging systems (e.g. LEADseeker™, Amersham Pharmacia Biotech) and Flow Cytometers (e.g. FACScalibur, Becton Dickinson).

The measured fluorescence is compared with fluorescence from control cells not exposed to the test agent and the effects, if any, of the test agent on gene expression modulated through the regulatory sequence is determined from the ratio of fluorescence in the test cells to the fluorescence in the control cells.

Where appropriate, a cell extract can be prepared using conventional methods.

Accordingly, in a seventh aspect of the invention, there is provided an assay method which comprises:

a) contacting a host cell extract with a dye compound comprising at least one $NO_2$ group wherein said host cell has been transfected with a nucleic acid molecule comprising expression control sequences operably linked to a sequence encoding a nitroreductase; and b) measuring an increase in fluorescence as a measure of nitroreductase gene expression.

In a particularly preferred embodiment, the dye compound is a cyanine dye compound comprising at least one $NO_2$ group. Suitably, the cyanine dye is a compound of Formula I as hereinbefore described.

In one embodiment of any of the previous aspects of the invention, increased fluorescence of the cyanine dye molecule is identified by analysis of fluorescence emission in the range 500 to 900 nm, preferably 550-780 nm, and, most preferably 665-725 nm.

In an eighth aspect of the invention there is provided a kit for a reporter system comprising a means for expressing a nitroreductase enzyme and a dye molecule comprising at least one $NO_2$ group.

Suitable means for expressing a nitroreductase enzyme include an expression plasmid or other expression construct. Methods for preparing such expression constructs are well known to those skilled in the art.

In a ninth aspect of the invention there is provided a kit for detecting the presence of one component of a specific binding pair comprising a nitroreductase enzyme coupled to the other component of said specific binding pair and a dye molecule comprising at least one $NO_2$ group.

In a preferred embodiment of the eighth or ninth aspect, the dye molecule is a cyanine dye molecule comprising at least one $NO_2$. Suitably, the cyanine dye is a compound of Formula I as hereinbefore described.

The change in fluorescence which arises from nitroreductase action on dye molecules comprising at least one $NO_2$, and particularly Cy-Q dyes, can be exploited in the construction of ratiometric fluorescence reporters or "cassettes" based on linked fluorophores one of which is a molecule such as a Cy-Q dye.

Accordingly, in a tenth aspect of the invention there is provided a paired fluorophore ratiometric reporter of Formula IV:

$$D_1 \text{—} L \text{—} D_2 \qquad (IV)$$

wherein:

$D_1$ is a detectable fluorophore;

$D_2$ is a cyanine dye molecule having Formula (I); and

L is a linker group.

Suitably, $D_1$ and $D_2$ are selected such that excitation of the cassette is at two different wavelengths, $\lambda 1$ and $\lambda 2$, where the wavelengths are chosen to be suitable to elicit fluorescence emission from the fluorophore $D_1$ (at wavelength $\lambda 3$) and the fluorophore corresponding to $D_2$ (at wavelength $\lambda 4$), and from which $D_2$ is derived, yet lacking the at least one $NO_2$ group.

In a particularly preferred embodiment, $D_2$ is selected from Cy3Q and Cy5Q.

In a preferred embodiment, L is a cleavable linker, for example, chemically cleavable, photocleavable (e.g. nitrobenzylalcohol) or enzymatically cleavable (e.g. ester, amide, phosphodiester, azo) by enzymes such as proteases. Suitable methods for cleaving such a linker are well known and described, for example, in Gerard Marriott et al., Preparation and photoactivation of caged fluorophores and caged proteins using a new cross-linking reagent, Bioconjugate Chemistry; (1998); 9(2); 143-151 and WO 00/75358.

In one embodiment, $D_1$ and $D_2$ may be in a FRET arrangement.

Preferably, the compound of Formula IV is rendered cell or membrane permeable.

In a particularly preferred embodiment of the tenth aspect, there is provided a compound of Formula V.

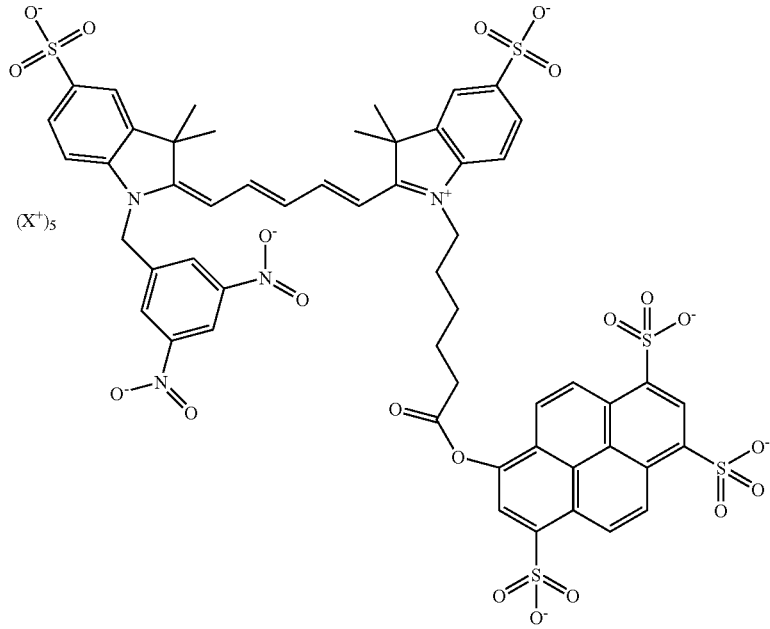

Formula V

In this embodiment, $D_1$ is 8-hydroxy-pyrene-1,3,6-trisulfonic acid (Cascade Blue™), $D_2$ is Cy5Q and L is an ester linkage.

In this embodiment, $D_1$ and $D_2$ are arranged in a FRET arrangement such that the fluorescence of $D_1$ is quenched by $D_2$. When the cassette of Formula V is incubated in the presence of intracellular enzymes (e.g. when the cassette is successfully transported into a cell) the linker, L, is cleaved thus releasing $D_1$ from the energy transfer arrangement and, when excited at wavelength λ1, fluorescence emission at wavelength λ3 can be detected. Under these conditions determination of the fluorescence emission at λ3 and comparison with the unreacted cassette will give a measure of the cleavage of the linker moiety, L (and, thus, a measure of uptake of the cassette into cells, for example). In the absence of nitroreductase, only low or zero emission from $D_2$ at wavelength λ4 will be detected. In the presence of nitroreductase the CyQ moiety is reduced to form a fluorescent form of Cy such that excitation at wavelength λ2 will give emission at wavelength λ4. Under these conditions, determination of the fluorescence emission at λ4 and comparison with the fluorescence emission at λ4 of the unreacted cassette will give a measure of the degree of conversion of $D_2$ into its reduced form and hence a measure of nitroreductase activity.

Suitably, the compound of Formula IV may be used in an assay method in accordance with any one of the third, fourth, fifth, sixth or eighth aspects of the invention.

SPECIFIC DESCRIPTION

For the purposes of clarity, certain embodiments of the present invention will now be described by way of example with reference to the following figures.

EXAMPLE 1

Figure 1:
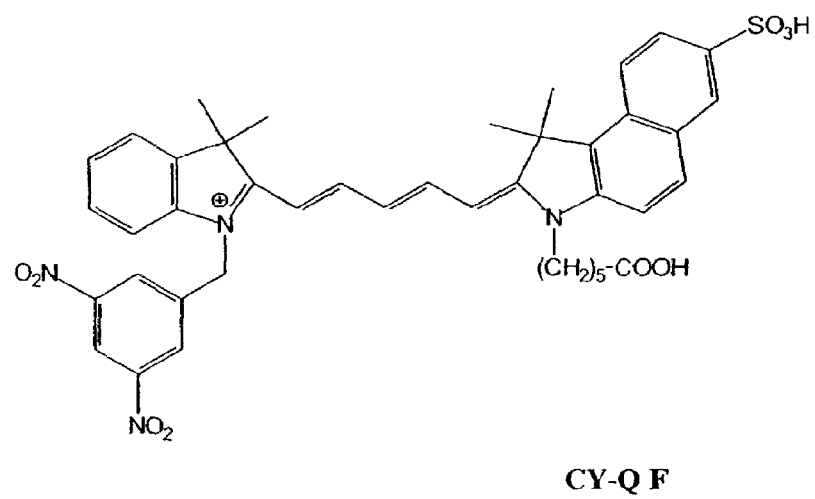
FIG. 1a shows the chemical structure of the compound of Formula II, termed Cy-Q F.
FIG. 1b shows a fluorescence emission spectrum of Cy-Q F incubated for various times in the presence of E. coli B nitroreductase.
Figure 1:
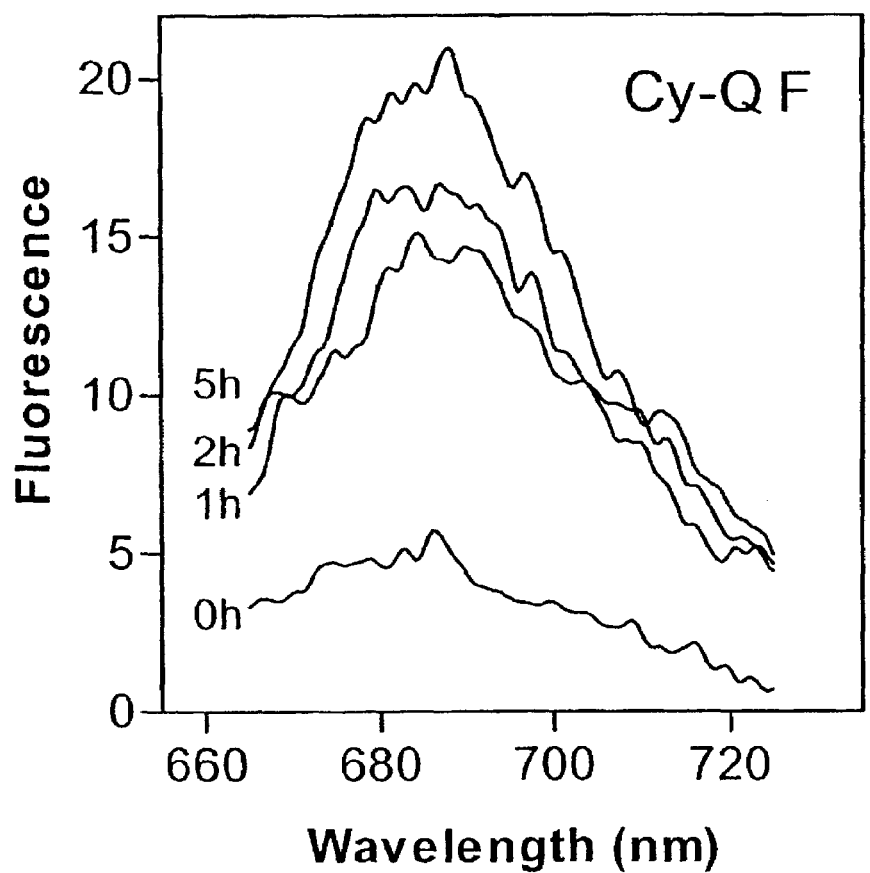

A reaction mixture was prepared containing 0.8 mg/ml E. coli B nitroreductase, 1 mM NADH, 0.4 μm FMN and 0.05 mM Cyanine-Q F (Cy-Q F, FIG. 1a) in phosphate buffered saline on ice. A sample was removed immediately for analysis by fluorescence spectroscopy, and further samples were removed for analysis after incubation of the reaction mixture at 37° C. for 1, 2, and 5 hours.

Analysis of fluorescence emission in the range 665 nm to 725 nm arising from excitation at 650 nm revealed a marked increase in fluorescence with time of incubation of Cy-Q F with nitroreductase (FIG. 1b), with a maximum emission at 690 nm.

EXAMPLE 2

Figure 2:
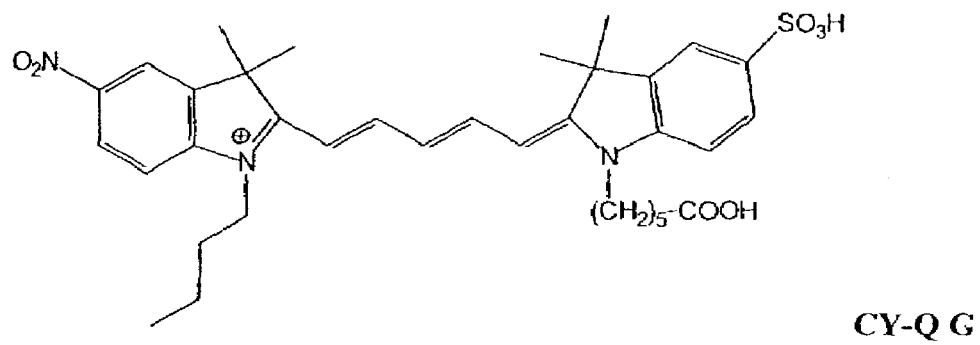
FIG. 2a shows the chemical structure of the compound of Formula III, termed Cy-Q G.
FIG. 2b shows a fluorescence emission spectrum of Cy-Q G incubated for various times in the presence of E. coli B nitroreductase.
Figure 2:
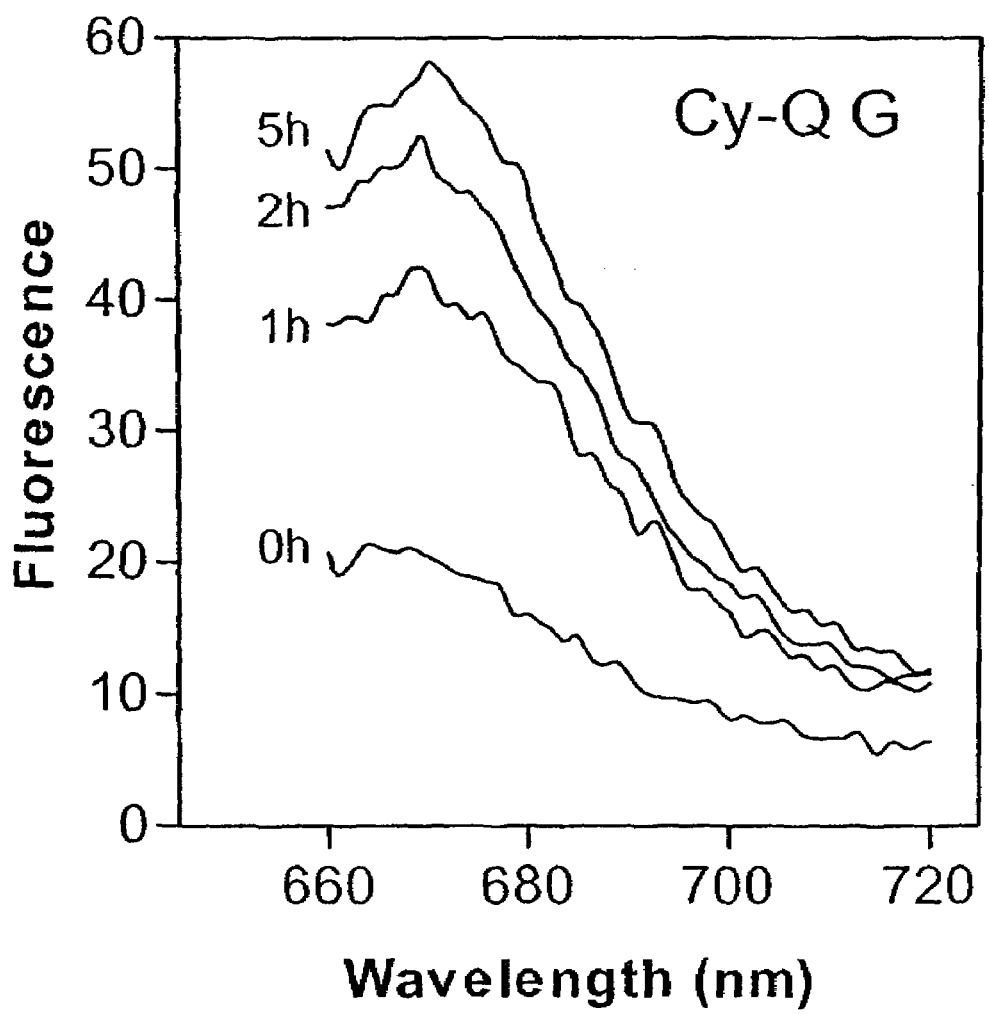

A reaction mixture was prepared containing 0.8 mg/ml E. coli B nitroreductase, 1 mM NADH, 0.4 μm FMN, and 0.05 mM Cyanine-Q F (Cy-Q G, FIG. 2a) in phosphate buffered saline on ice. A sample was removed immediately for analysis by fluorescence spectroscopy, and further samples were removed for analysis after incubation of the reaction mixture at 37° C. for 1, 2, and 5 hours.

Analysis of fluorescence emission in the range 660 nm to 720 nm arising from excitation at 650 nm revealed a marked increase in fluorescence with time of incubation of Cy-Q G with nitroreductase (FIG. 2b), with a maximum emission at 675 nm.

Figure 3A:
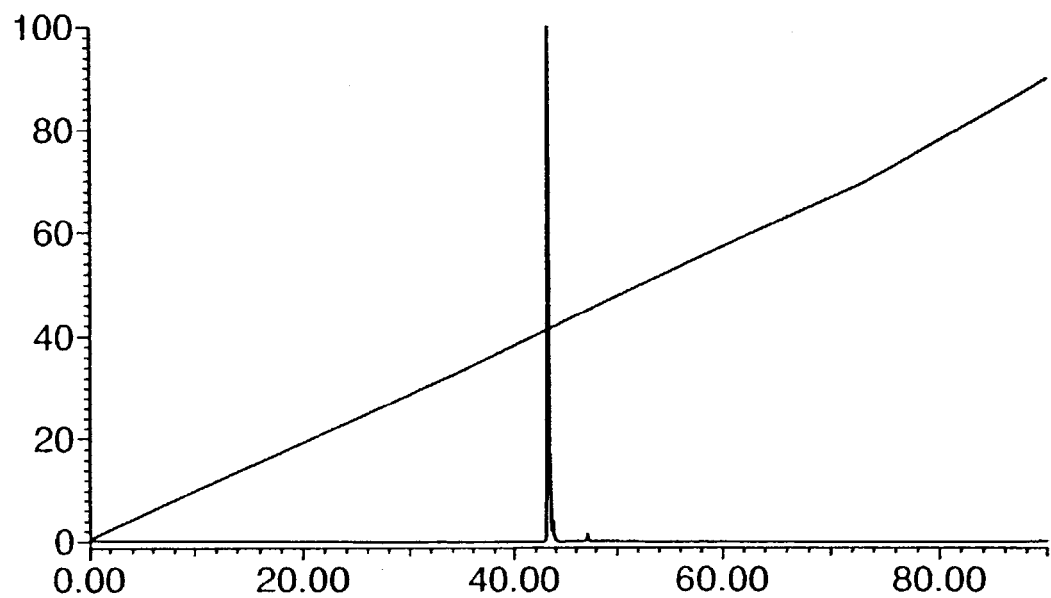
FIG. 3a shows HPLC analysis of Cy-Q G.
Figure 3B:
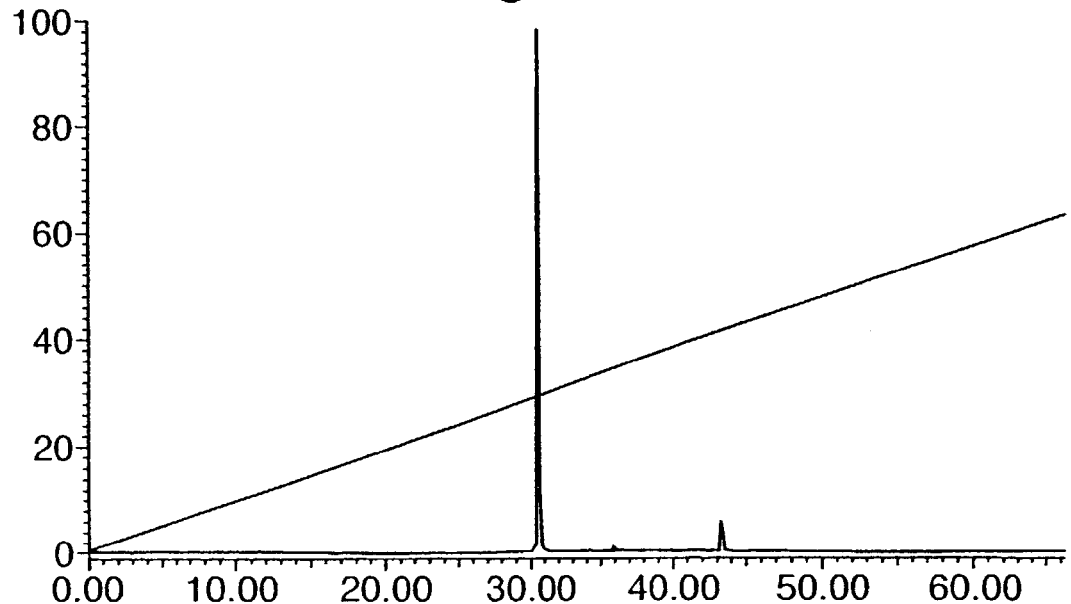
FIG. 3b shows HPLC analysis of Cy-Q G treated with nitroreductase.
Figure 4A:
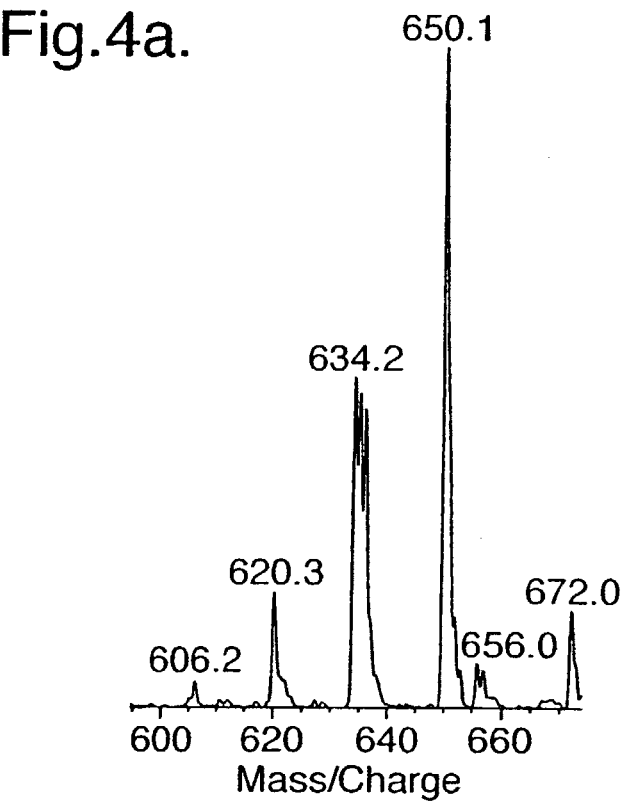
FIG. 4a shows MALDI-TOF Mass Spectrometry analysis of Cy-Q G.
Figure 4B:
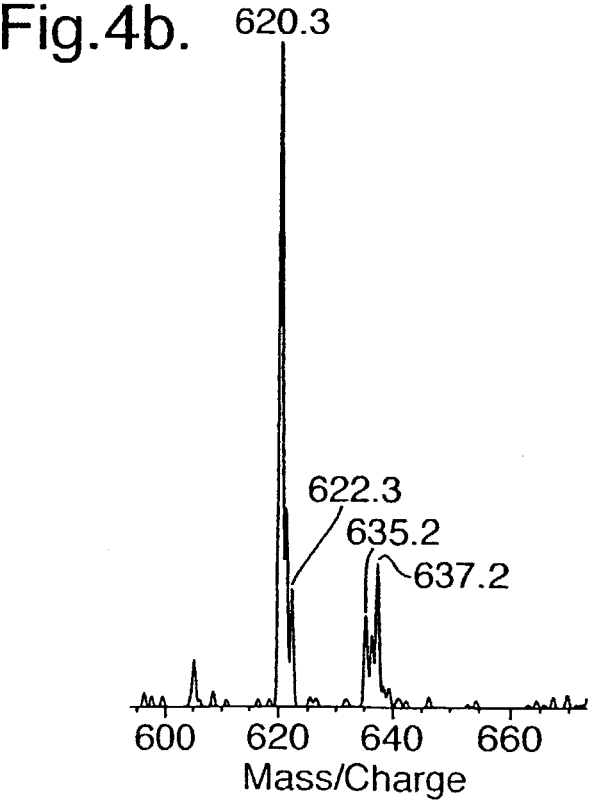
FIG. 4b shows MALDI-TOF Mass Spectrometry analysis of Cy-Q G treated with nitroreductase.
Figure 5:
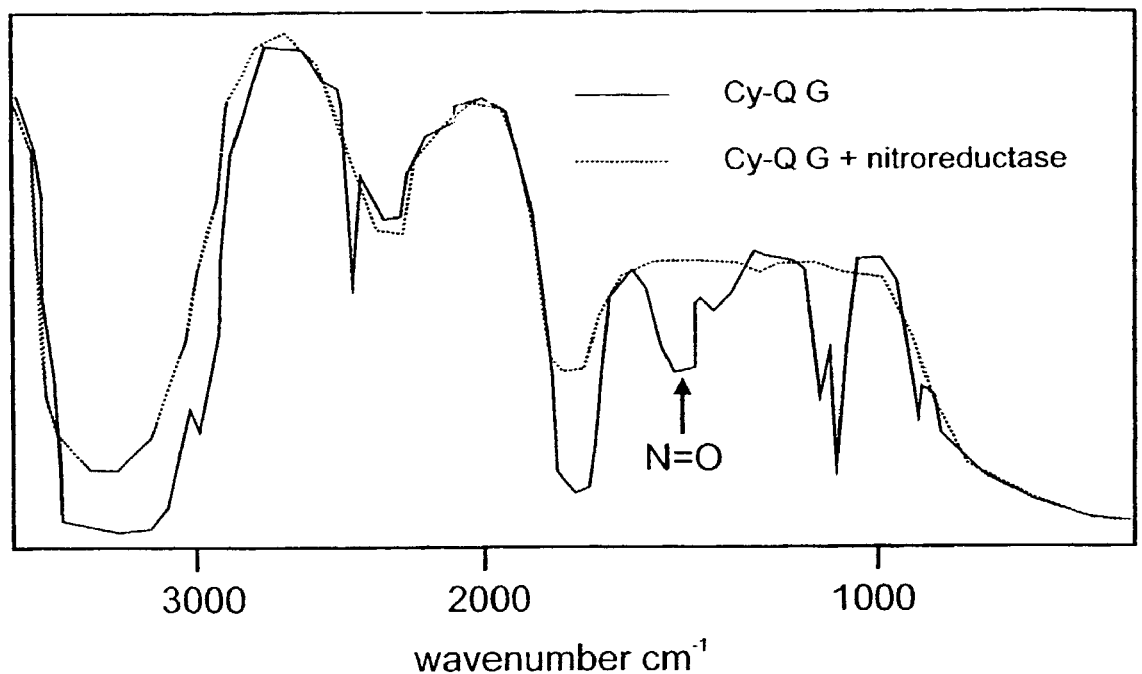
FIG. 5 shows infra-red absorbtion spectroscopy of Cy-Q G and Cy-Q G treated with nitroreductase.

Samples of Cy-Q G incubated in the presence and absence of nitroreductase were analysed by HPLC. The HPLC results (FIGS. 3a and 3b) indicate that nitroreductase treatment of the Cy-Q gives >95% conversion of the Cy-Q G to a product with an HPLC retention time of 30.5 minutes, compared to a retention time of 43.2 minutes for the starting material. The major peaks from the HPLC analysis were subjected to further analysis by MALDI-TOF mass spectrometry (FIGS. 4a and 4b). This analysis showed a principal mass of 620.3 for the reaction product, compared to 650.1 for the Cy-Q G starting material, this mass change is consistent with the conversion of a —$NO_2$ group to a —$NH_2$ group, and is consistent with the proposed enzyme reaction mechanism. This was confirmed by further analysis using infra-red absorption spectroscopy (FIG. 5) which showed the disappearance of a strong N=O bond absorption band on enzyme treatment, consistent with the enzymatic reduction of the Cy-Q G —$NO_2$ group to an amine group.

EXAMPLE 3

Nitroreductase $K_m$ Measurement for Cy5Q

Figure 6:
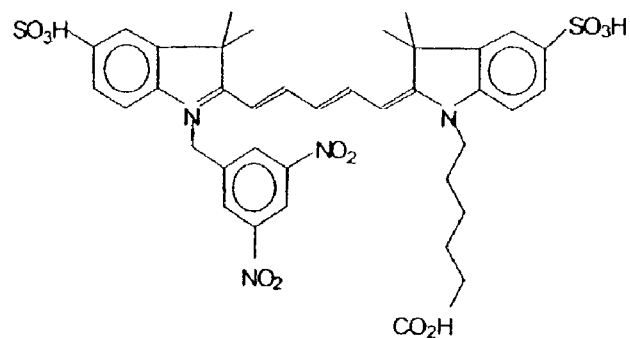
FIG. 6 shows the chemical structure of Cy5Q.

E. coli B nitroreductase (500 ng) was incubated in the presence of increasing concentrations of Cy5Q (FIG. 6) in 200 μl of 10 mM Tris.HCl pH 7.5 containing 1 mM NADH and incubated at room temperature for 30 minutes.

Figure 7:
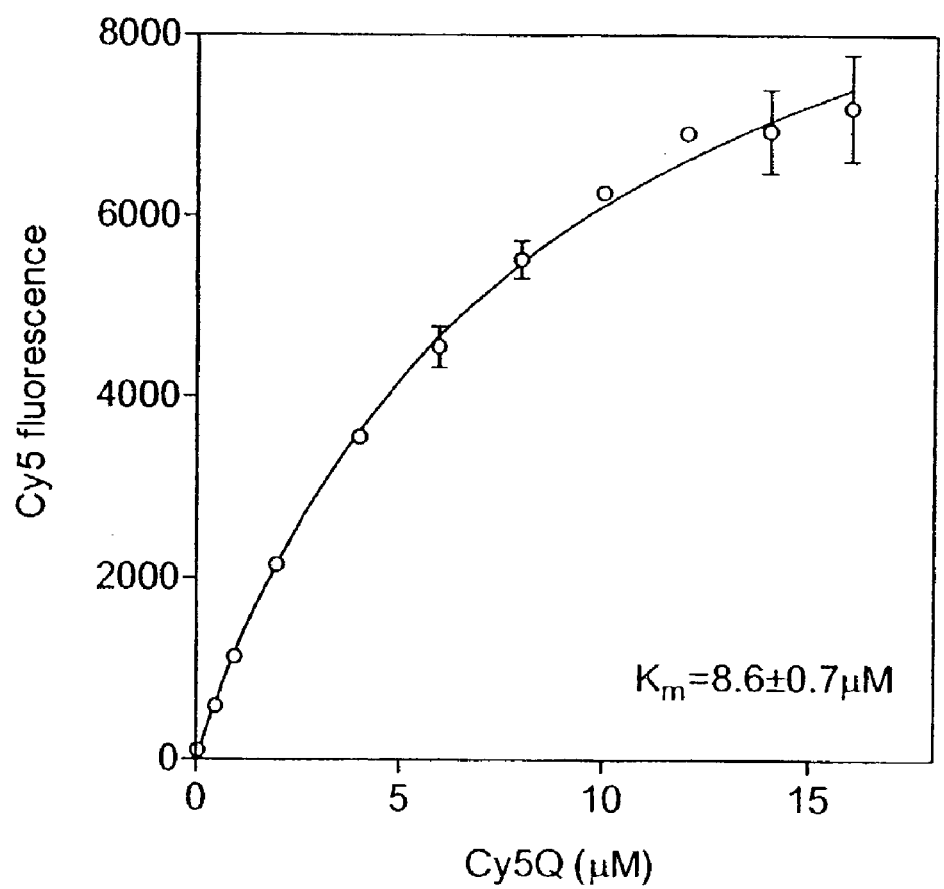
FIG. 7 shows fluorescence emission different concentration of Cy5Q in the presence nitroreductase.

Fluorescence from each reaction was measured in a CytoStar (PerSeptive Biosystems) plate reader using 610/20 nm excitation and 670/40 nm emission filters. Results were corrected for fluorescence in the absence of nitroreductase enzyme (FIG. 7) and a $K_m$ value of 8.6±0.7 μM was calculated using curve fitting software (Prism).

EXAMPLE 4

In-Vitro Binding Assay with Nitroreductase

Nitroreductase (400 ug, 16.7 nmol) was labelled with 334 nmol Sulpho-NHS-biotin (Pierce) in PBS pH 8.0 for 2 hours on ice. Free biotin was removed by dialysis overnight against PBS pH 7.4 at 4° C.

Increasing concentrations of biotin (Sigma) from 0-100 nmol/well were added to duplicate wells of a streptavidin-coated microtitre plate (Pierce) in 100 ul PBS pH 7.4, followed by 100 ul of PBS containing 0.5 ug biotinylated nitroreductase, and the plate incubated for 1 hour at room temperature.

Following incubation the plate was washed three times with PBS to remove unbound enzyme and 100 ul of 5 uM Cy5Q in PBS containing 1 mM NADH was added to all wells.

After incubation for 35 minutes at room temperature to allow reaction between bound nitroreductase and the added Cy5Q the plate was analysed on a Cytofluor plate reader (Perseptive) using a 610/20 nm excitation filter and a 670/40 nm emission filter.

Figure 8:
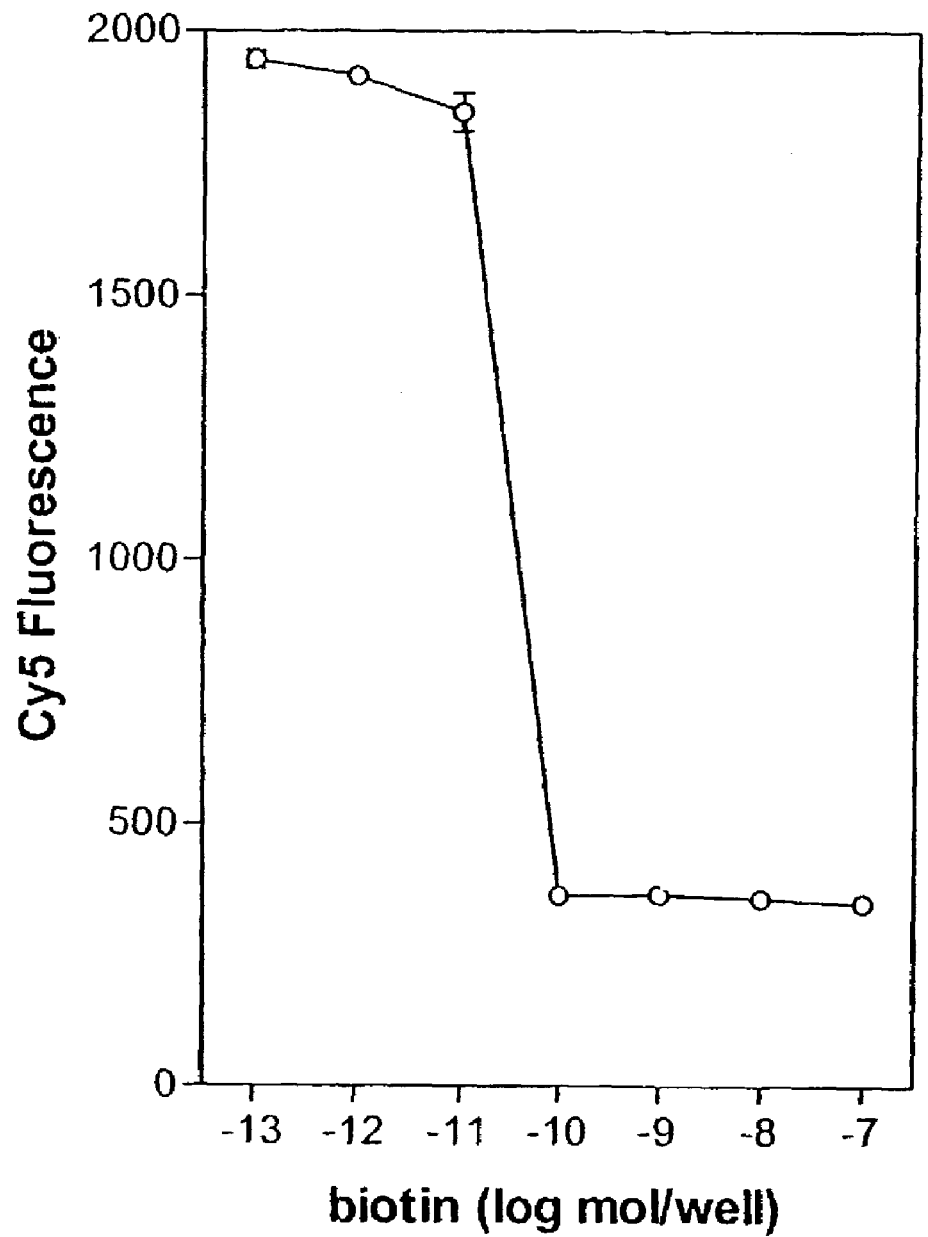
FIG. 8 shows the results of an in vitro binding assay with nitroreductase.

FIG. 8 shows high fluorescence of Cy5 in the presence of bound nitroreductase. Binding of nitroreductase to the plate was displaced in high concentrations of free biotin thus Cy5Q was not reduced and shows low fluorescence.

EXAMPLE 5

Transfection of Nitroreductase and Measurement of Activity in Cell Lysates

The *E. coli* nitroreductase B gene was cloned into the p-Target mammalian expression vector (Promega) under the control of a CMV promoter and transfected into CHO cells using Effectene (Qiagen) transfection reagent according to the suppliers instructions.

Figure 9:
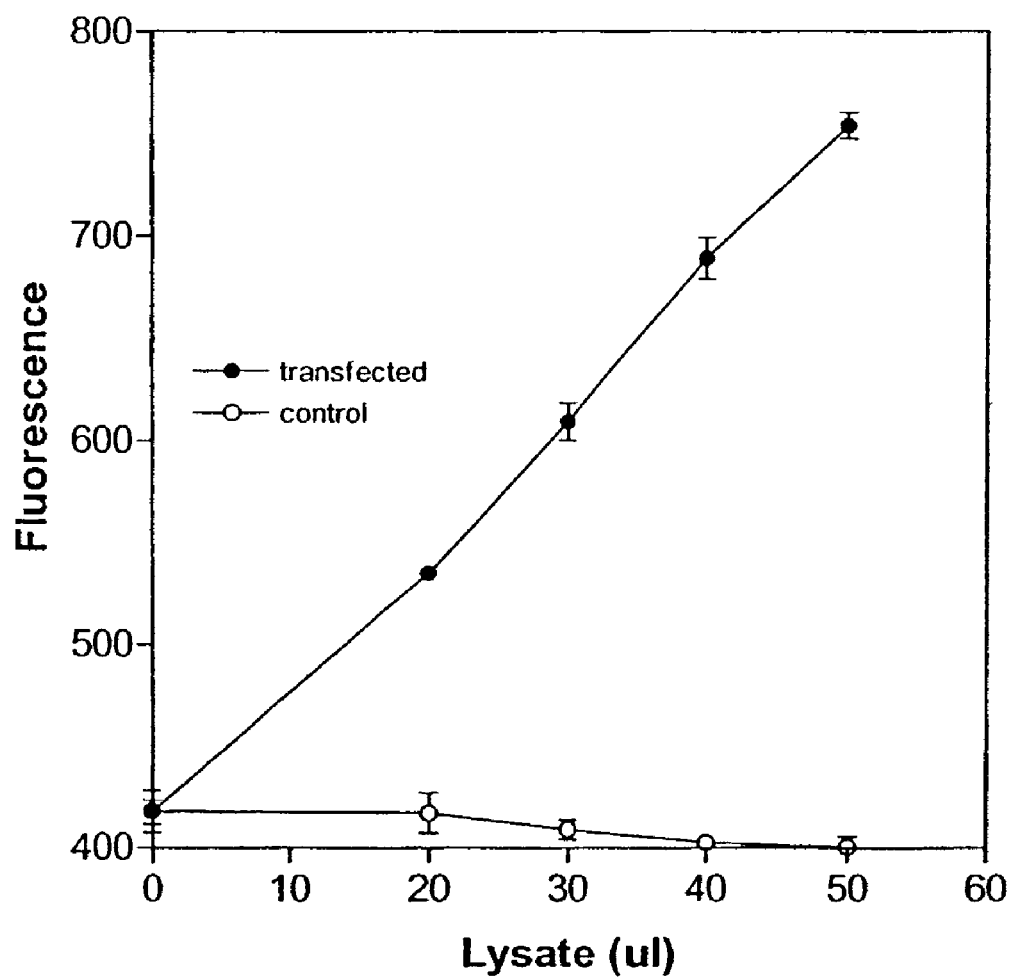
FIG. 9 shows detection of nitroreductase activity in cell lysates from transfected and control cells by detecting Cy5 fluorescence.

Following growth of cells for 24 hours cell lysates were prepared from transfected and non-transfected control cells by sonication in phosphate buffered saline. Nitroreductase activity was determined by addition of 2 μM Cy5Q and incubating at room temperature for 90 minutes followed by measurement of fluorescence in a CytoStar (PerSeptive Biosystems) plate reader (FIG. 9) using 610/20 nm excitation and 670/40 nm emission filters. Results showed a strong increase in fluorescence in lysate samples from nitroreductase expressing cells which was proportional to the amount of cell lysates assayed.

EXAMPLE 6

Measurement of Cellular Nitroreductase Activity Using Cell Permeable Fluorescence Substrates Two ethyl-ester derivatives of nitro-quenched cyanine dyes, Cy3Qee (Formula IIIa) and Cy5Qee (Formula IIIb) were synthesised.

Preparation of 5-(Carboxymethyl)-1,2,3,3-tetramethyl-3H-indolium Iodide (1)

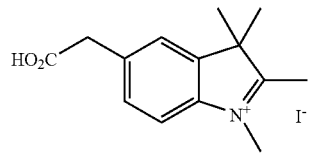

(1)

Methyl iodide (3 ml, 48.19 mmol) was added to a solution of 2,3,3-trimethyl-3H-indol-5-yl-acetic acid (2.5 g, 11.52 mmol) in sulfolan (15 ml). The reaction was heated at 48° C. for 18 hours, then cooled to room temperature. The crude reaction mixture was added dropwise to an excess of diethyl ether and the precipitate was collected by filtration and dried in vacuo to obtain the product as a beige solid (3.27 g, 79% yield). $^1$H NMR (d$_6$-DMSO): δH 7.85 (d, 1H), 7.70 (s, 1H), 7.50 (d, 1H), 3.95 (s, 3H), 3.75 (s, 2H), 2.75 (s, 3H), 1.50 (s, 6H). MALDI-TOF, m/z 232 (M$^+$=232 for $C_{14}H_{18}NO_2$).

Preparation of 1-(3,5-dinitrobenzyl)-5-(carboxymethyl)-3H-indolium Bromide (2)

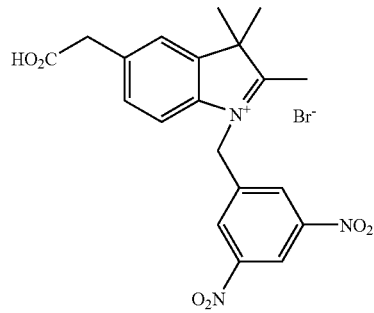

(2)

3,5-Dinitrobenzyl chloride (12.46 g, 57.5 mmol) was added to a solution of 2,3,3-trimethyl-3H-indol-5-yl-acetic acid (2.5 g, 11.5 mmol) with sodium bromide (5.92 g, 57.5 mmol) in sulfolan (10 ml). The reaction was heated at 100° C. for 20 hrs, then cooled to room temperature. The crude reaction mixture was added dropwise to an excess of ethyl acetate and the dark brown solid was filtered OFF and dissolved in dimethylsulfoxide before purification by reverse phase chromatography. The product was isolated as beige solid (54% yield). $^1$H NMR (d$_6$-DMSO): δH: 8.75 (s, 1H), 8.45 (s, 2H), 7.15 (s, 1H), 6.95 (d, 1H), 6.70 (d, 2H), 5.10 (s, 2H), 3.95 (s, 2H), 3.45 (s, 3H), 1.40 (s, 6H). MALDI-TOF, m/z=398 (M$^+$=398 for $C_{20}H_{20}N_3O_6$).

Preparation of 5-(Carboxymethyl)-2-{(1E,3E)-5-[6-(carboxymethyl)-1,1,3-trimethyl-1,3-dihydro-2H-indol-2-ylidene]-1,3-pentadienyl}-1-(3,5-dinitrobenzyl)-3,3-dimethyl-3H-indolium Salt (3)

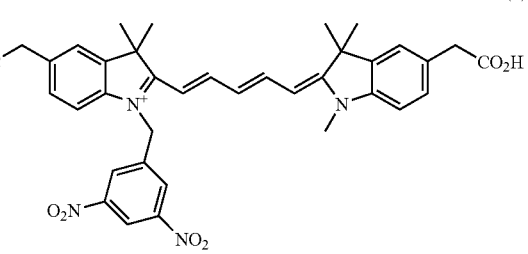

(3)

1,2,3-tetramethyl-3H-indolium iodide (1) (50 mg, 0.139 mmol) and 1-(3,5-dinitrobenzyl)-5-(carboxymethyl)-3H-indolium bromide (2) (66 mg, 0.139 mmol) were dissolved in acetic acid (3.15 ml), pyridine (3.15 ml) and acetic anhydride (0.7 ml) with malonaldehydebis(phenylimine) monohydrochloride (358 mg, 1.39 mmol). The reaction was heated at 70° C. for 2 hrs. The solution was then added dropwise to an excess of diethyl ether and the blue solid was filtered off and purified by reverse phase chromatography (HPLC with water/ 0.1% trifluoroacetic acid and acetonitrile/0.1% trifluoroacetic acid as eluent). The product was isolated as a dark blue powder (33.3 mg, 31% yield). $UV_{max}$ ($H_2O$)=646 nm. $^1$H NMR ($d_6$-DMSO): δH 8.75 (s, 1H), 8.45 (s, 2H), 8.35 (m, 2H), 7.5 (m, 6H), 6.55 (m, 2H), 6.25 (d, 1H), 5.6 (s, 2H), 3.7 (m, 7H), 1.8 (s, 3H), 1.7 (s, 2H). $FAB^+$: m/z=665 ($M^+$=665 for $C_{37}H_{37}N_4O_8$).

Preparation of 1-(3,5-dinitrobenzyl)-5-(2-ethoxy-2-oxoethyl)-2-{(1E,3E)-5-[6-(2-ethoxy-2-oxoethyl)-1,1,3-trimethyl-1,3-dihydro-2H-indol-2-ylidene]-1,3-pentadienyl}-3,3-dimethyl-3H-indoluim Salt (4) (Formula IIIa)

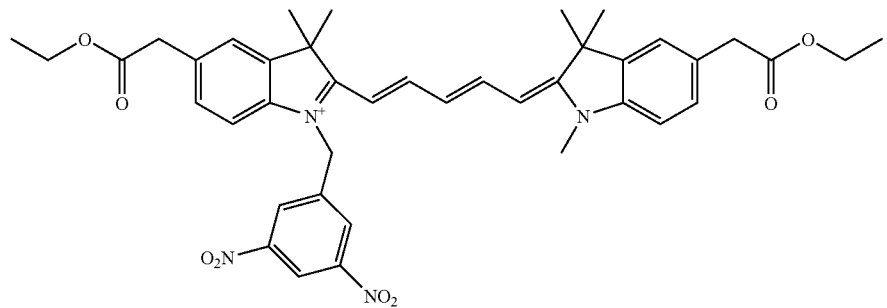

(4)

5-(Carboxymethyl)-2-{(1E,3E)-5-[6-(carboxymethyl)-1,1,3-trimethyl-1,3-dihydro-2H-indol-2-ylidene]-1,3-pentadienyl}-1-(3,5-dinitrobenzyl)-3,3-dimethyl-3H-indolium (3) (4.5 mg, 0.0058 mmol) was dissolved in ethanol (2 ml) with concentrated hydrochloric acid (2011) and stirred at room temperature under nitrogen for 16 hrs. The solvent was removed under reduced pressure and the residue purified by reverse phase chromatography (HPLC with water/0.1% trifluoroacetic acid and acetonitrile/0.1% trifluoroacetic acid as eluent) to isolate the product as a blue solid (4.1 mg, 85% yield). $UV_{max}$ ($H_2O$)=647 nm. $^1$H NMR ($CDCl_3$): δH 8.95 (s, 1H), 8.4 (s, 2H), 7.85 (m, 2H), 7.3 (m, 6H), 6.85 (d, 1H), 6.5 (m, 2H), 5.5 (s, 2H), 4.2 (q, 4H), 3.7 (s, 4H), 3.65 (s, 3H), 1.8 (s, 3H), 1.7 (s, 3H), 1.25 (t, 6H). $FAB^+$: m/z=721 ($M^+$=721 for $C_{41}H_{46}N_4O_8$).

Preparation of 5-{2-[(acetyloxy)methoxy]-2-oxoethyl}-2-[(1E,3E)-5-(6-{2-[(acetyloxy)methoxy]-2-oxoethyl}-1,1,3-trimethyl-1,3-dihydro-2H-indol-2-ylidene)-1,3-pentadienyl]-1-(3,5-dinitrobenzyl)-3,3-dimethyl-3H-indolium salt (5)

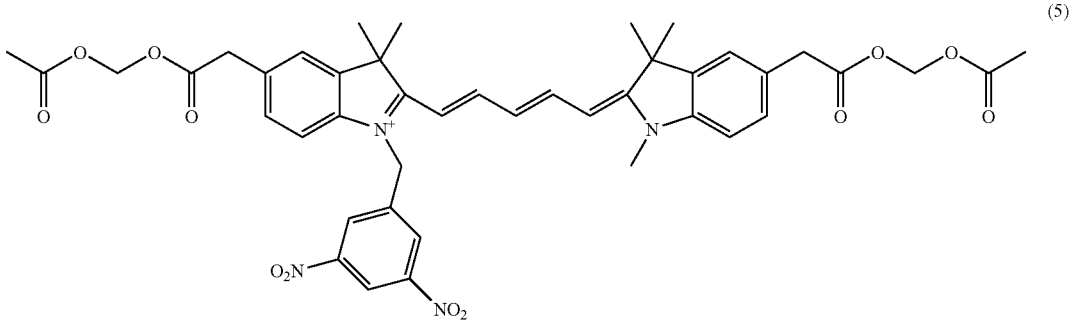

(5)

To a solution of 5-(Carboxymethyl)-2-{(1E,3E)-5-[6-(carboxymethyl)-1,1,3-trimethyl-1,3-dihydro-2H-indol-2-ylidene]-1,3-pentadienyl}-1-(3,5-dinitrobenzyl)-3,3-dimethyl-3H-indolium (3) (10 mg, 0.015 mmol) in anhydrous acetonitrile (2 ml) with N,N-diisopropylethylamine (4.7 mg, 0.0375 mmol) was added bromomethylacetate (23 mg, 0.150 mmol). The reaction was stirred at room temperature under a nitrogen atmosphere for 24 hours. The solvent was then evaporated under reduced pressure and the blue residue was purified by reverse phase chromatography (HPLC). The product was isolated as a blue powder (10.6 mg, 83% yield). $UV_{max}$ ($H_2O$)=643 mm. $^1$H NMR ($CDCl_3$): δH 9.05 (s, 1H), 8.5 (s, 2H), 8.35 (m, 1H), 7.35 (m, 6H), 7.2 (m, 1H), 7.0 (m, 1H), 6.45 (m, 1H), 6.15 (m, 1H), 5.75 (s, 2H), 3.75 (s, 3H), 3.7 (s, 4H), 2.1 (s, 3H), 1.05 (s, 3H), 1.75 (s, 6H), 1.70 (s, 6H). $FAB^+$: m/z=809 ($M^+$=809 for $C_{43}H_{45}N_4O_{12}$).

Preparation of 5-(Carboxymethyl)-2-{(1E)-3-[6-(carboxymethyl)-1,1,3-trimethyl-1,3-dihydro-2H-indol-2-ylidene]-1-propenyl}-1-(3,5-dinitrobenzyl)-3,3-dimethyl-3H-indolium salt (6)

(6)

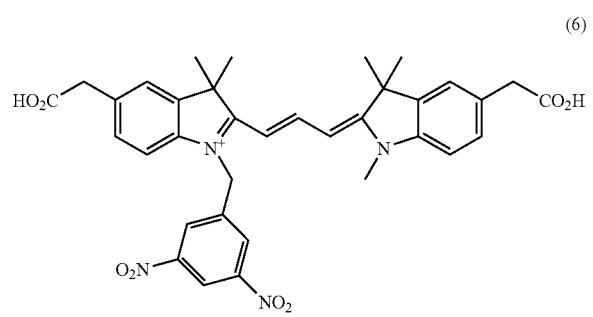

1,2,3,3-tetramethyl-3H-indolium iodide (1) (100 mg, 0.28 mmol) and 1-(3,5-dinitrobenzyl)-5-(carboxymethyl)-3H-indolium bromide (2) (133 mg, 0.28 mmol) were dissolved in acetic acid (2.25 ml), pyridine (2.25 ml) and acetic anhydride (0.25 ml) with N,N'-diphenylformamidine (55 mg, 0.28 mmol). The reaction was heated at 70° C. for 2 hrs. The solution was then added dropwise to an excess of diethyl ether and the red solid was filtered then purified by reverse phase chromatography (HPLC with water/0.1% trifluoroacetic acid and acetonitrile/0.1% trifluoroacetic acid as eluent). The product was isolated as a dark pink powder (16.5 mg, 8% yield). $UV_{max}$ ($H_2O$)=553 nm. MALDI-TOF: m/z=640 ($M^+$=639 for $C_{35}H_{35}N_4O_8$).

Preparation of 1-(3,5-dinitrobenzyl)-5-(2-ethoxy-2-oxoethyl)-2-{(1E)-3-[6-(2-ethoxy-2-oxoethyl)-1,1,3-trimethyl-1,3-dihydro-2H-indol-2-ylidene]-1-propenyl}-3,3-dimethyl-3H-indoluim salt (7) (Formula IIIb)

(7)

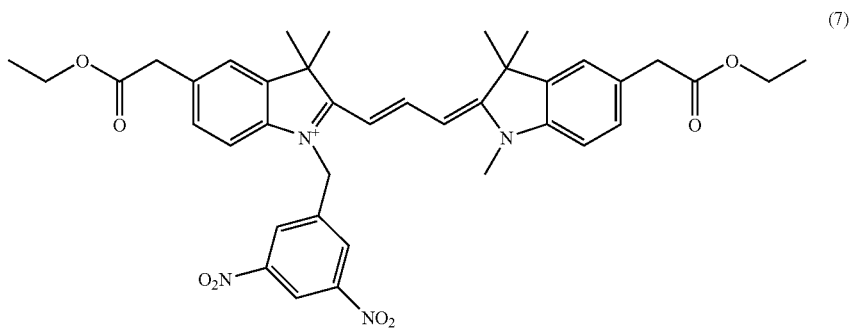

5-(Carboxymethyl)-2-{(1E)-3-[6-(carboxymethyl)-1,1,3-trimethyl-1,3-dihydro-2H-indol-2-ylidene}-1-propenyl}-1-(3,5-dinitrobenzyl)-3,3-dimethyl-3H-indolium (6) (4 mg, 0.00531 mmol) was dissolved in ethanol (2 ml) with concentrated hydrochloric acid (50 μl) and stirred at room temperature under nitrogen for 20 hrs. The solvent was removed under reduced pressure and the residue was purified by reverse phase chromatography (HPLC with water/0.1% trifluoroacetic acid and acetonitrile/0.1% trifluoroacetic acid as eluent) to isolate the product as a pink solid (3.2 mg, 74% yield). $UV_{max}$ ($H_2O$)=549 nm. $^1$H NMR ($CDCl_3$): δH 9.0 (s, 1H), 8.4 (s, 2H), 8.45 (m, 1H), 7.3 (m, 6H), 6.9 (d, 1H), 6.45 (m, 1H), 5.6 (s, 2H), 4.2 (q, 4H), 3.75 (s, 4H), 3.7 (s, 3H), 1.85 (s, 3H), 1.7 (s, 3H), 1.3 (t, 6H). MALDI TOF: m/z=696 ($M^+$=695 for $C_{39}H_{43}N_4O_8$).

Cy3Qee (Formula IIIa) and Cy5Qee (Formula IIIb) were evaluated as cell permeable fluorescence substrates for nitroreductase measurement in living cells. Nitroreductase expressing cells and control cells were cultured at 10,000 cells/well in 96 well plates in tissue culture medium containing 10% foetal calf serum and incubated at 37° C. in the presence of 10 μM Cy3Qee or 30 μM Cy5Qee. Fluorescence measurements were made using a CytoStar (PerSeptive Biosystems) plate reader using 530/25 nm excitation and 580/50 nm emission filters for Cy3Qee and 610/20 nm excitation and 670/40 nm emission filters for Cy5Qee.

Figure 10:
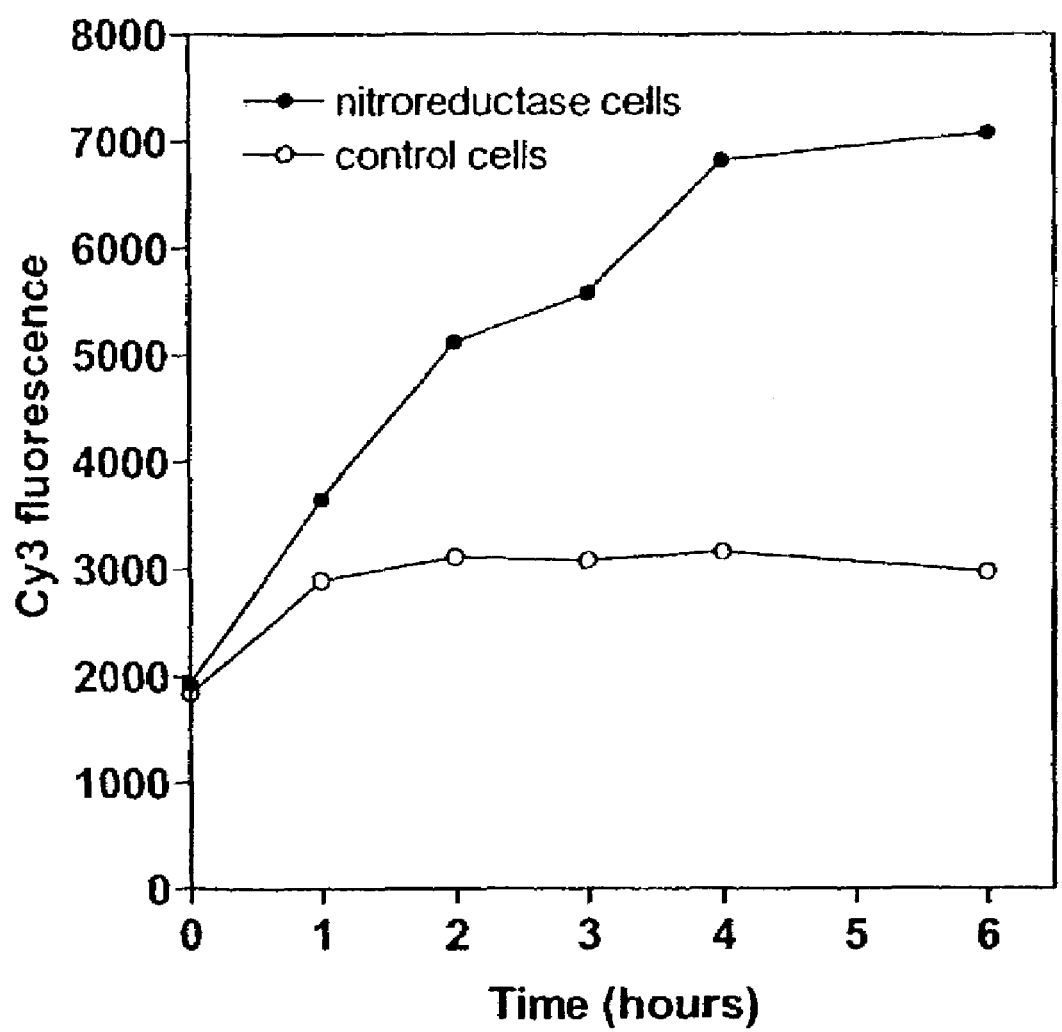
FIG. 10 shows Cy3 fluorescence in cells expressing nitroreductase and control cells.
Figure 11:
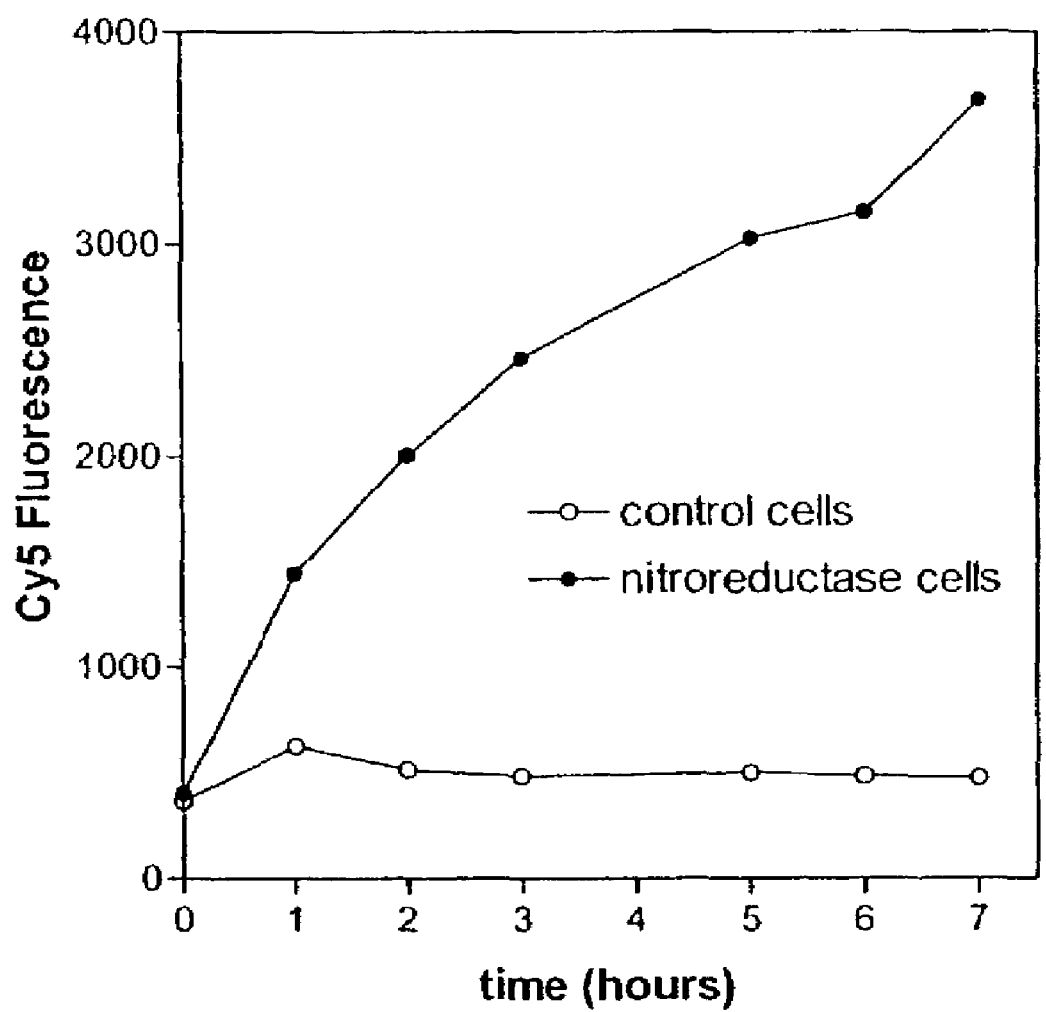
FIG. 11 shows Cy5 fluorescence in cells expressing nitroreductase and control cells.

Fluorescence measurements showed a significant time dependent increase in fluorescence in nitroreductase expressing cells with minimal changes in fluorescence in control cells indicating that both Cy3Qee (FIG. 10) and Cy5Qee (FIG. 11) are effective cell permeable substrates for measurement of nitroreductase activity in living cells.

EXAMPLE 7

Measurement of Cellular Nitroreductase Activity in Living Cells by Flow Cytometry Nitroreductase expressing cells and control cells were incubated for 2 hours at 37° C. in tissue culture media containing 30 μM Cy3Qee. Following incubation cells were washed with phosphate buffered saline and trypsinised to produce cell suspensions for flow cytometry.

Figure 12:
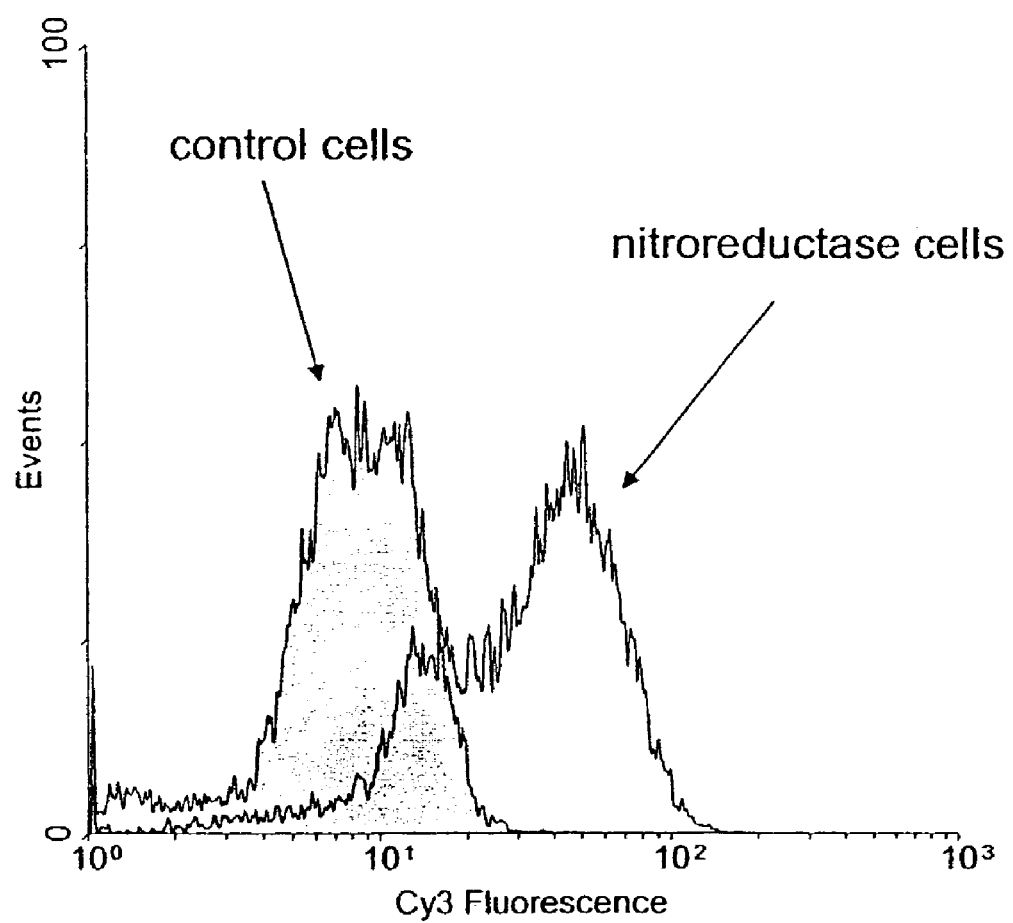
FIG. 12 shows measurement of cellular nitroreductase activity by flow cytometry.

Cells were analysed using a FACScalibur flow cytometer (Becton Dickinson) using 488 nm laser excitation and a 585/42 nm emission filter. Results (FIG. 12) show a significant increase in fluorescence in nitroreductase expressing cells (mean fluorescence 169.9) compared with control cells (mean fluorescence 18.2).

EXAMPLE 8

Preparation of Cy5™-Cascade Blue® Ester Linked Cassette

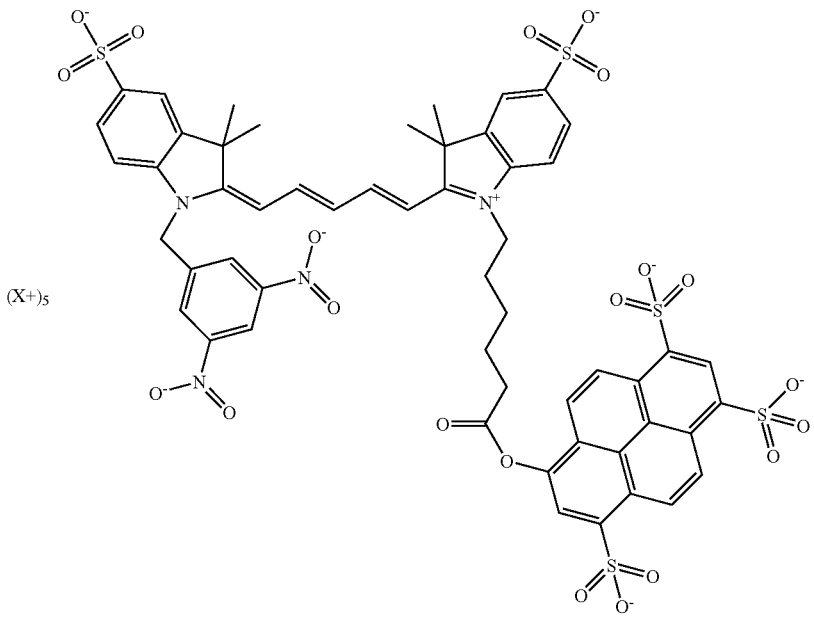

Cy5Q mono free acid potassium salt (obtained from Amersham Pharmacia Biotech Ltd) (5 mg, 0.006 mmol), Cascade blue 0 (Molecular Probes) (8-hydroxypyrene-1,3,6-trisulfonic acid sodium salt (8.8 mg, 0.018 mmol) (Fluka)), N, N diisopropylcarbodiimide (10 µl, 0.065 mmol), 1-hydroxybenzotriazole (1 mg, 0.007 mmol), 4-(dimethylamino)pyridine (0.9 mg, 0.007 mmol) and activated molecular sieves powder (250 mg) were stirred together in anhydrous N,N-dimethylformamide (2 ml) at room temperature for 12 hrs. A new product spot was observed by TLC (RP $C_{18}$ 1:1 MeOH: Water), rf=0.8 (compared to free Cy5Q; rf=0.72). The molecular sieves were filtered off and the product precipitated into diethyl ether. The precipitate was filtered off, washed with ethyl acetate and dried. The product was purified by RP $C_{18}$ flash column chromatography. Unreacted 8-hydroxypyrene-1,3,6-trisulfonic acid sodium salt was eluted from the column with water and the product then eluted with 5% acetonitrile/water. Fractions containing pure product were collected and the majority of the solvent removed under reduced pressure. The residue was freeze dried to give the product as a cyan powder (1 mg, 11%).

λmax (Water) 648 nm (Cy5Q) 354, 372 nm (pyrene).

MALDI-TOF MS; found 1246 (MH⁺); [theoretical ($C_{54}H_{44}N_4O_{21}S_5$) 1245].

Figure 13:
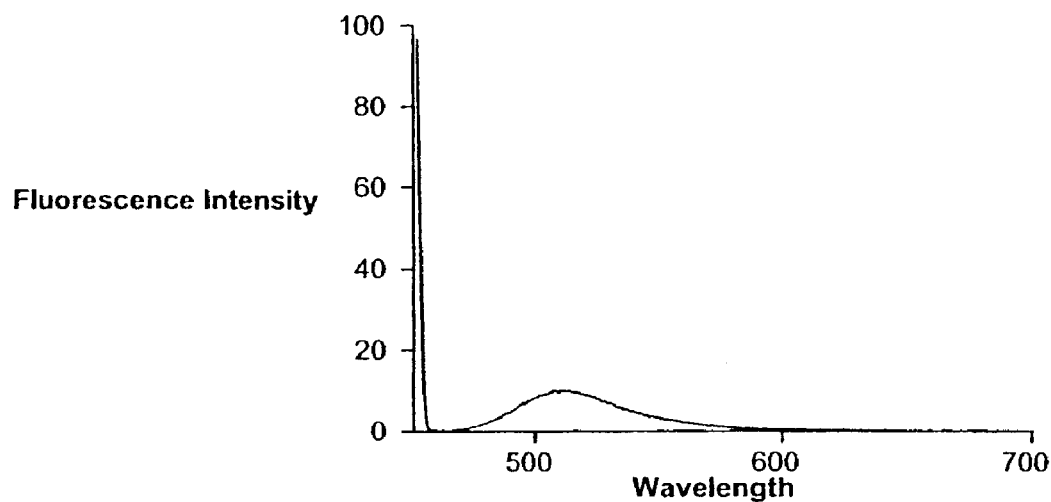
FIG. 13 shows fluorescence emission spectrum of Cy5Q-cascade blue cassette, a=1 at 649 nm in water, then diluted 100 microliters+3 ml water, excitation 450 nm.
Figure 14:
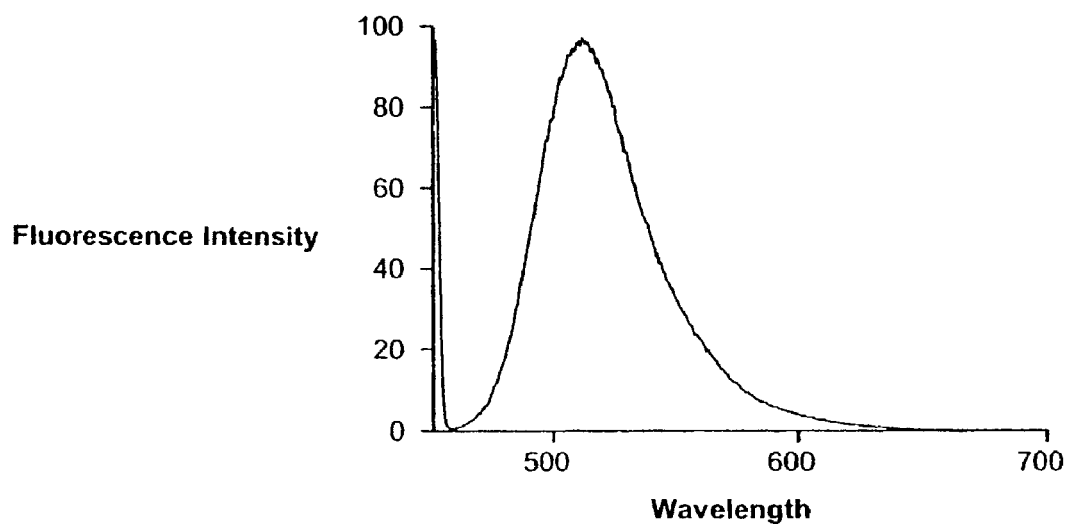
FIG. 14 shows fluorescence emission spectrum of 8-hydroxy-pyrene-1,3,6-trisulfonic acid a=0.2 at 455 nm in water, then diluted 100 microliters+3 ml water, excitation 450 nm.
Figure 15:
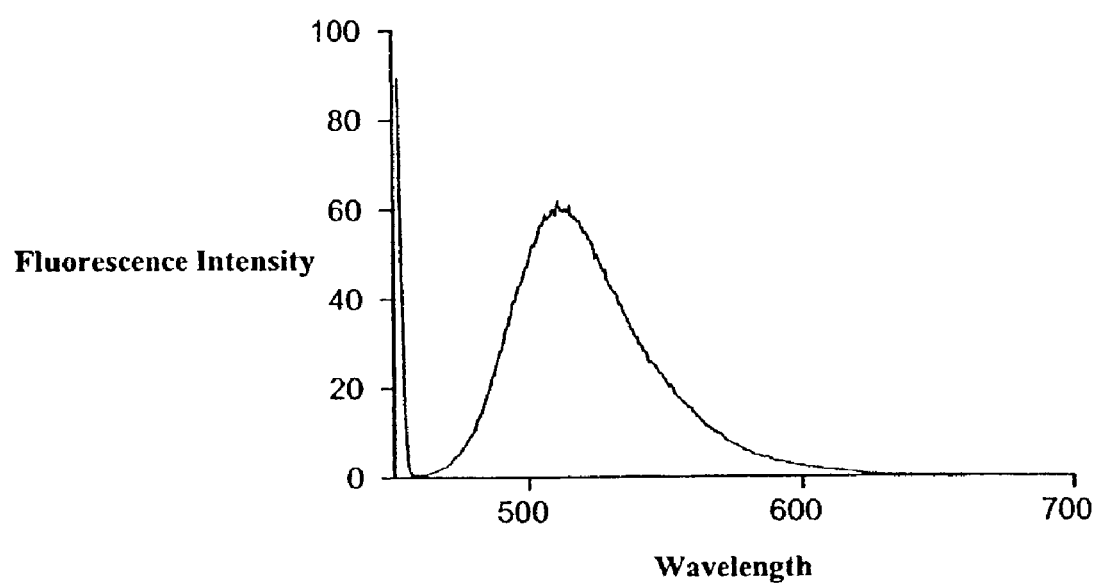
FIG. 15 shows Cy5Q-cascade blue cassette after treatment with NaOH solution, a=1 at 650 nm in water, then diluted 100 microliters+3 ml water, excitation 450 nm.

Fluorescence; Cy5Q-Cascade blue ester linked cassette has negligible emission at 510 nm (FIG. 13); 510 nm is the emission maxima for free 8-hydroxypyrene-1,3,6-trisulfonic acid sodium salt in water, (FIG. 14). This indicates efficient energy transfer from Cascade blue to Cy5Q and quenching of the fluorescence of the Cascade blue moiety when bound to Cy5Q within the cassette. When treated with sodium hydroxide solution, fluorescence emission at 510 nm is observed (FIG. 15), indicating the chemical hydrolysis of the ester linkage and the liberation of the fluorescent 8-hydroxypyrene-1,3,6-trisulfonic moiety.

In Vitro Evaluation

Cy5Q-Cascade blue cassette (0.8 mM in acetate buffer pH 5.0) was diluted to 811M in PBS pH 7.4 containing 1 mM NADH. A cell lysate was prepared from $2\times10^7$ SKOV cells by re-suspension of scraped cells in 5 ml PBS at 4° C. and repeated passage through a 25 gauge syringe needle. Aliquots (1 ml) of Cy5Q-Cascade blue were incubated with 500 µl of cell lysate or PBS for 20 minutes at 37° C. Following incubation 100 µl of a 1 ng/µl solution of $E.$ $coli$ B nitroreductase was added to one sample and incubation continued for 5 minutes. Aliquots (100 ml) were then dispensed in quadruplicate from each sample to a 96 well plate for measurement of fluorescence on a Cytofluor plate reader using 450 nm excitation/530 nm emission filters for cascade blue and 610 nm excitation/670 nm emission for Cy5.

Figure 16:
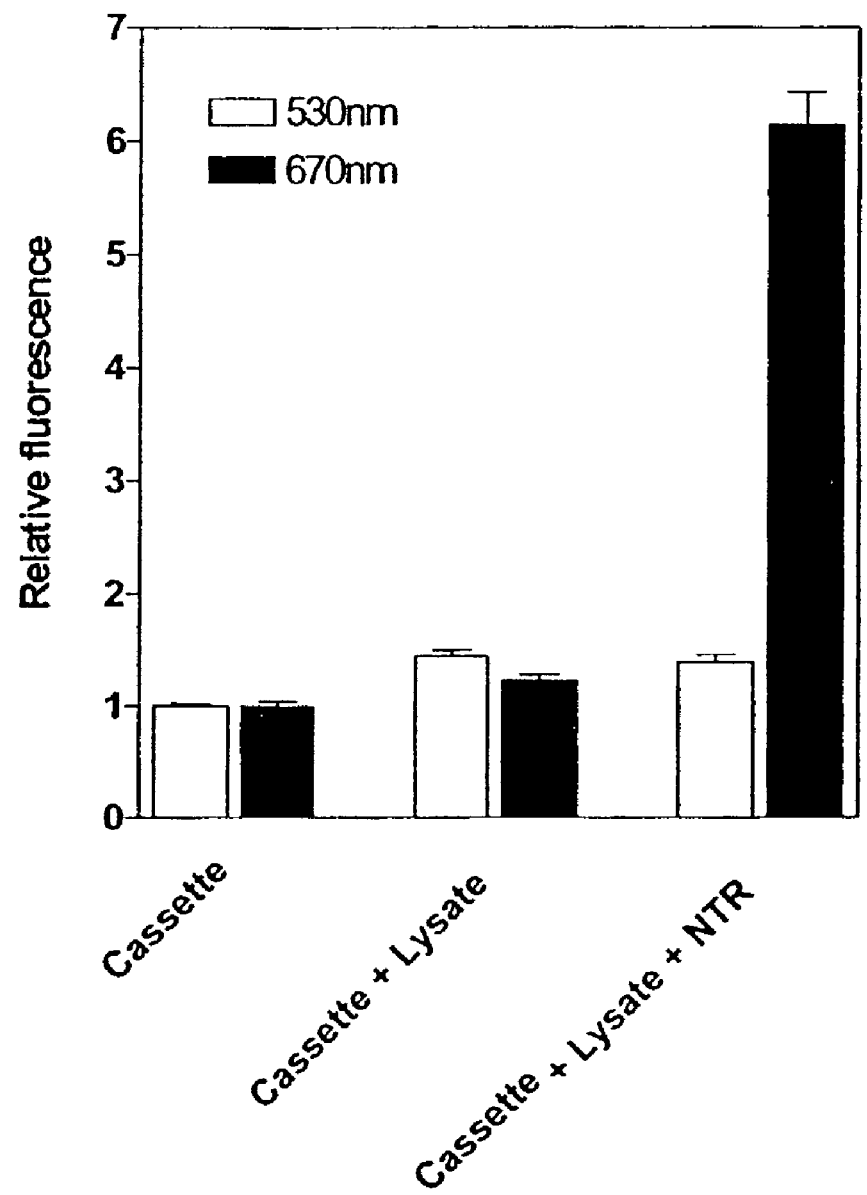
FIG. 16 shows relative fluorescence of Cy5Q-cascade blue cassette in the presence of absence of lysate/NTR.

FIG. 16 shows an increase of fluorescence emission at 530 nm (i.e. of Cascade Blue) when the cassette is incubated in the presence of cell lysate and an increase in fluorescence emission at 670 nm (i.e. Cy5) when nitroreductase enzyme is present.

What is claimed is:

1. A method for increasing the fluorescence of a cyanine dye molecule which includes at least one $NO_2$ group, comprising reducing said at least one $NO_2$ group of said cyanine dye to NHOH or $NH_2$ in a nitroreductase reporter gene assay; wherein the cyanine dye molecule is of Formula Ia, Formula Ib or Formula Ic:

Formula Ia

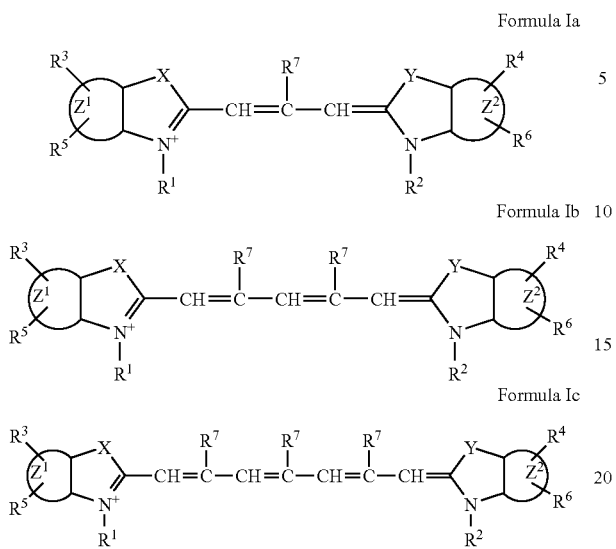

Formula Ib

Formula Ic wherein groups $R^3$, $R^4$, $R^5$ and $R^6$ are attached to the rings containing X and Y or, optionally, are attached to atoms of the $Z^1$ and $Z^2$ ring structures;

$Z^1$ and $Z^2$ each represent a bond or the atoms necessary to complete one or two fused aromatic rings each ring having five or six atoms, selected from the group consisting of carbon atoms, oxygen atoms, nitrogen atoms and sulphur atoms wherein no more than two atoms in each ring are oxygen, nitrogen, or sulphur;

X and Y independently represent a carbon atom substituted with two C1-C4 alkyl residues that may be linked to form a C4-C5 ring system or are selected from the group consisting of oxygen, sulphur, selenium, —CH═CH— and N—W wherein N is nitrogen and W is selected from hydrogen, a group —$(CH_2)_m R^8$ where m is an integer from 1 to 26 and $R^8$ is selected from the group consisting of hydrogen, amino, aldehyde, acetal, ketal, halo, cyano, aryl, heteroaryl, hydroxyl, sulphonate, sulphate, carboxylate, phosphonate, polyethylene glycol, substituted amino, quaternary ammonium, nitro, primary amide, substituted amide, and groups reactive with amino, hydroxyl, carbonyl, carboxyl, phosphoryl, and sulphydryl groups;

groups $R^3$, $R^4$, $R^5$, $R^6$ and $R^7$ are independently selected from the group consisting of hydrogen, substituted or unsubstituted $C_1$-$C_4$ alkyl, $OR^9$, $COOR^9$, nitro, amino, acylamino, quaternary ammonium, phosphate, sulphonate and sulphate, where $R^9$ is substituted or unsubstituted and selected from H, $C_1$-$C_4$ alkyl, amino, aldehyde, acetal, ketal, halo, cyano, aryl, heteroaryl, hydroxyl, sulphonate, sulphate, carboxylate, substituted amino, quaternary ammonium, nitro, primary amide, substituted amide, and groups reactive with amino, hydroxyl, carbonyl, carboxyl, phosphoryl, and sulphydryl groups;

groups $R^1$ and $R^2$ are $C_1$-$C_{10}$ alkyl which may be unsubstituted or substituted;

and further wherein at least one of the groups $R^1$, $R^2$, $R^3$, $R^4$, $R^5$, $R^6$ and $R^7$ includes at least one nitro group which reduces the fluorescence emission of said dye such that it is essentially non-fluorescent.

2. A method for increasing the fluorescence of a cyanine dye molecule which includes at least one $NO_2$ group, comprising reducing said at least one $NO_2$ group of said cyanine dye to NHOH or $NH_2$ in a nitroreductase reporter gene assay; wherein the cyanine dye molecule is a compound of Formula II or Formula III, or salts thereof Formula II

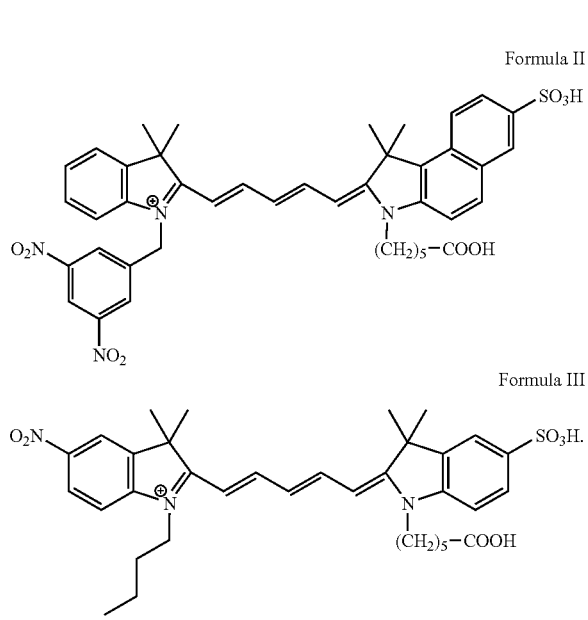

Formula III

3. A method for detecting nitroreductase enzyme activity in a composition comprising:
  a) mixing said composition with a cyanine dye molecule under conditions to promote nitroreductase activity; and
  b) measuring an increase in fluorescence wherein the increase is a measure of the amount of nitroreductase activity;
further wherein said cyanine dye molecule is of Formula Ia, Formula Ib or Formula Ic:

Formula Ia

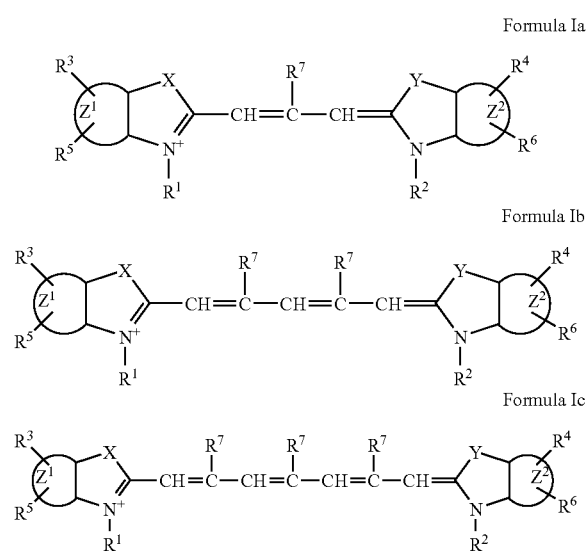

Formula Ib

Formula Ic wherein groups $R^3$, $R^4$, $R^5$ and $R^6$ are attached to the rings containing X and Y or, optionally, are attached to atoms of the $Z^1$ and $Z^2$ ring structures;

$Z^1$ and $Z^2$ each represent a bond or the atoms necessary to complete one or two fused aromatic rings each ring having five or six atoms, selected from the group consisting of carbon atoms, oxygen atoms, nitrogen atoms and sulphur atoms wherein no more than two atoms in each ring are oxygen, nitrogen, or sulphur;

X and Y independently represent a carbon atom substituted with two C1-C4 alkyl residues that may be linked to form a C4-C5 ring system or are selected from the group consisting of oxygen, sulphur, selenium, —CH=CH— and N—W wherein N is nitrogen and W is selected from hydrogen, a group —(CH$_2$)$_m$R$^8$ where m is an integer from 1 to 26 and R$^8$ is selected from the group consisting of hydrogen, amino, aldehyde, acetal, ketal, halo, cyano, aryl, heteroaryl, hydroxyl, sulphonate, sulphate, carboxylate, phosphonate, polyethylene glycol, substituted amino, quaternary ammonium, nitro, primary amide, substituted amide, and groups reactive with amino, hydroxyl, carbonyl, carboxyl, phosphoryl, and sulphydryl groups;

groups R$^3$, R$^4$, R$^5$, R$^6$ and R$^7$ are independently selected from the group consisting of hydrogen, substituted or unsubstituted C$_1$-C$_4$ alkyl, OR$^9$, COOR$^9$, nitro, amino, acylamino, quaternary ammonium, phosphate, sulphonate and sulphate, where R$^2$ is substituted or unsubstituted and selected from H, C$_1$-C$_4$ alkyl, amino, aldehyde, acetal, ketal, halo, cyano, aryl, heteroaryl, hydroxyl, sulphonate, sulphate, carboxylate, substituted amino, quaternary ammonium, nitro, primary amide, substituted amide, and groups reactive with amino, hydroxyl, carbonyl, carboxyl, phosphoryl, and sulphydryl groups;

groups R$^1$ and R$^2$ are C$_1$-C$_{10}$ alkyl which may be unsubstituted or substituted;

and further wherein at least one of the groups R$^1$, R$^2$, R$^3$, R$^4$, R$^5$, R$^6$ and R$_7$ includes at least one nitro group which reduces the fluorescence emission of said dye such that it is essentially non-fluorescent.

4. The method of claim 3 wherein the composition comprises a cell or cell extract.

5. An assay method which comprises:
a) contacting a host cell or host cell extract with a cyanine dye molecule, wherein said host cell has been transfected with a nucleic acid molecule comprising expression control sequences operably linked to a sequence encoding a nitroreductase; and
b) measuring an increase in fluorescence as a measure of nitroreductase gene expression;
wherein said cyanine dye molecule is of Formula Ia, Formula Ib or Formula Ic:

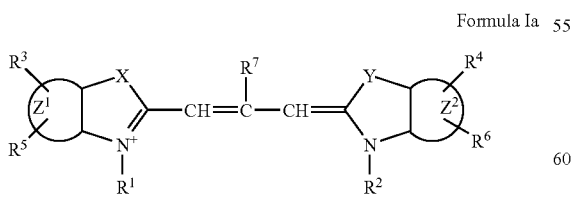

Formula Ia

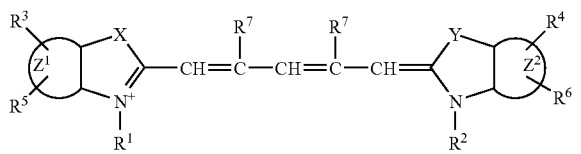

Formula Ib

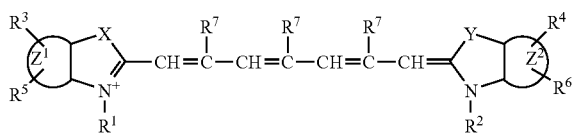

Formula Ic wherein groups R$^3$, R$^4$, R$^5$ and R$^6$ are attached to the rings containing X and Y or, optionally, are attached to atoms of the Z$^1$ and Z$^2$ ring structures;

Z$^1$ and Z$^2$ each represent a bond or the atoms necessary to complete one or two fused aromatic rings each ring having five or six atoms, selected from the group consisting of carbon atoms, oxygen atoms, nitrogen atoms and sulphur atoms wherein no more than two atoms in each ring are oxygen, nitrogen, or sulphur;

X and Y independently represent a carbon atom substituted with two C1-C4 alkyl residues that may be linked to form a C4-C5 ring system or are selected from the group consisting of oxygen, sulphur, selenium, —CH=CH— and N—W wherein N is nitrogen and W is selected from hydrogen, a group —(CH$_2$)$_m$R$^8$ where m is an integer from 1 to 26 and R$^8$ is selected from the group consisting of hydrogen, amino, aldehyde, acetal, ketal, halo, cyano, aryl, heteroaryl, hydroxyl, sulphonate, sulphate, carboxylate, phosphonate, polyethylene glycol, substituted amino, quaternary ammonium, nitro, primary amide, substituted amide, and groups reactive with amino, hydroxyl, carbonyl, carboxyl, phosphoryl, and sulphydryl groups;

groups R$^3$, R$^4$, R$^5$, R$^6$ and R$^7$ are independently selected from the group consisting of hydrogen, substituted or unsubstituted C$_1$-C$_4$ alkyl, OR$^9$, COOR$^9$, nitro, amino, acylamino, quaternary ammonium, phosphate, sulphonate and sulphate, where R$^9$ is substituted or unsubstituted and selected from H, C$_1$-C$_4$ alkyl, amino, aldehyde, acetal, ketal, halo, cyano, aryl, heteroaryl, hydroxyl, sulphonate, sulphate, carboxylate, substituted amino, quaternary ammonium, nitro, primary amide, substituted amide, and groups reactive with amino, hydroxyl, carbonyl, carboxyl, phosphoryl, and sulphydryl groups;

groups R$^1$ and R$^2$ are C$_1$-C$_{10}$ alkyl which may be unsubstituted or substituted;

and further wherein at least one of the groups R$^1$, R$^2$, R$^3$, R$^4$, R$^5$, R$^6$ and R$^7$ includes at least one nitro group which reduces the fluorescence emission of said dye such that it is essentially non-fluorescent.

6. The assay method of claim 5, wherein at least one of R$^1$ to R$^7$ of the cyanine dye molecule comprises an acetoxymethyl ester or a pivaloyl ester group.

* * * * *